US012733911B2

(12) United States Patent
Takada et al.

(10) Patent No.: US 12,733,911 B2
(45) Date of Patent: Sep. 15, 2026

(54) ULTRASOUND DIAGNOSTIC APPARATUS

(71) Applicant: Canon Kabushiki Kaisha, Tokyo (JP)

(72) Inventors: Yuko Takada, Utsunomiya (JP); Masaki Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 362 days.

(21) Appl. No.: 17/657,825

(22) Filed: Apr. 4, 2022

(65) Prior Publication Data

US 2022/0313220 A1 Oct. 6, 2022

(30) Foreign Application Priority Data

Apr. 5, 2021 (JP) ................................ 2021-064204
Mar. 24, 2022 (JP) ................................ 2022-048858

(51) Int. Cl.
*A61B 8/00* (2006.01)
*G06T 7/70* (2017.01)
*G06V 10/25* (2022.01)

(52) U.S. Cl.
CPC .............. *A61B 8/5215* (2013.01); *G06T 7/70* (2017.01); *G06V 10/25* (2022.01); *A61B 8/461* (2013.01);

(Continued)

(58) Field of Classification Search
CPC ........ G06V 10/25; G06V 10/82; A61B 8/085; A61B 8/469; A61B 8/5223; A61B 8/5215; A61B 8/461; A61B 6/5217; A61B 5/7264; A61B 5/748; A61B 6/469; A61B 8/463; A61B 8/488; A61B 8/5207; G06T 7/70; G06T 2207/10132; G06T 2207/20084;

(Continued)

(56) References Cited

U.S. PATENT DOCUMENTS

2012/0232375 A1* 9/2012 Zebaze ..................... G06T 7/70 600/407
2015/0190120 A1* 7/2015 Huang .................. A61B 8/485 600/438

(Continued)

FOREIGN PATENT DOCUMENTS

JP 2014-73303 A 4/2014
JP 2015-171425 A 10/2015

(Continued)

OTHER PUBLICATIONS

English translation of Li et al. (WO 2021/218077) (Year: 2021).*

(Continued)

*Primary Examiner* — Katherine L Fernandez
(74) *Attorney, Agent, or Firm* — Oblon, McClelland, Maier & Neustadt, L.L.P.

(57) ABSTRACT

According to one embodiment an ultrasound diagnostic apparatus includes processing circuitry. The processing circuitry acquires first ultrasonic image data of a first mode, estimates a position of an examination target included in the first ultrasonic image data by applying a trained model to the first ultrasonic image data and output an estimation result, calculates a coordinate of a region of interest corresponding to a second mode different from the first mode based on the estimation result and information on the second mode, and displays the region of interest on second ultrasonic image data of the second mode based on the coordinate.

26 Claims, 16 Drawing Sheets

(52) U.S. Cl.
CPC ............... *G06T 2207/10132* (2013.01); *G06T 2207/20084* (2013.01)

(58) Field of Classification Search
CPC ....................... G06T 2207/20081; G06T 7/73; G06T 7/0012
See application file for complete search history.

(56) References Cited

U.S. PATENT DOCUMENTS

| | | | | |
|---|---|---|---|---|
| 2015/0342561 | A1* | 12/2015 | Takeda | A61B 8/0841 600/443 |
| 2016/0022238 | A1* | 1/2016 | Park | A61B 6/5217 600/407 |
| 2017/0124426 | A1* | 5/2017 | Li | G16H 50/30 |
| 2017/0156702 | A1 | 6/2017 | Park et al. | |
| 2019/0125295 | A1* | 5/2019 | Tek | G16H 40/63 |
| 2020/0134825 | A1 | 4/2020 | Li et al. | |
| 2020/0397409 | A1* | 12/2020 | Inoue | A61B 8/5246 |
| 2022/0139531 | A1* | 5/2022 | Wang | G16H 50/20 382/128 |
| 2023/0225711 | A1* | 7/2023 | Dickie | A61B 8/465 600/453 |

FOREIGN PATENT DOCUMENTS

| | | | |
|---|---|---|---|
| JP | 2019/187649 | A1 | 10/2019 |
| JP | 2020-68797 | A | 5/2020 |
| WO | WO-2021218077 | A1 * | 11/2021 |

OTHER PUBLICATIONS

Office Action issued Jun. 30, 2025, in corresponding Chinese Patent Application No. 202210348632.1, 7 pages.
Japanese Office Action issued Nov. 18, 2025 in Japanese Patent Application No. 2022-048858, 3 pages.
Office Action issued Apr. 10, 2026, in corresponding Chinese Patent Application No. 202210348632.1, citing document 1 herein, 14 pages.
Office Action issued Apr. 21, 2026, in corresponding Japanese Patent Application No. 2022-048858, citing document 2 herein, 8 pages.

* cited by examiner

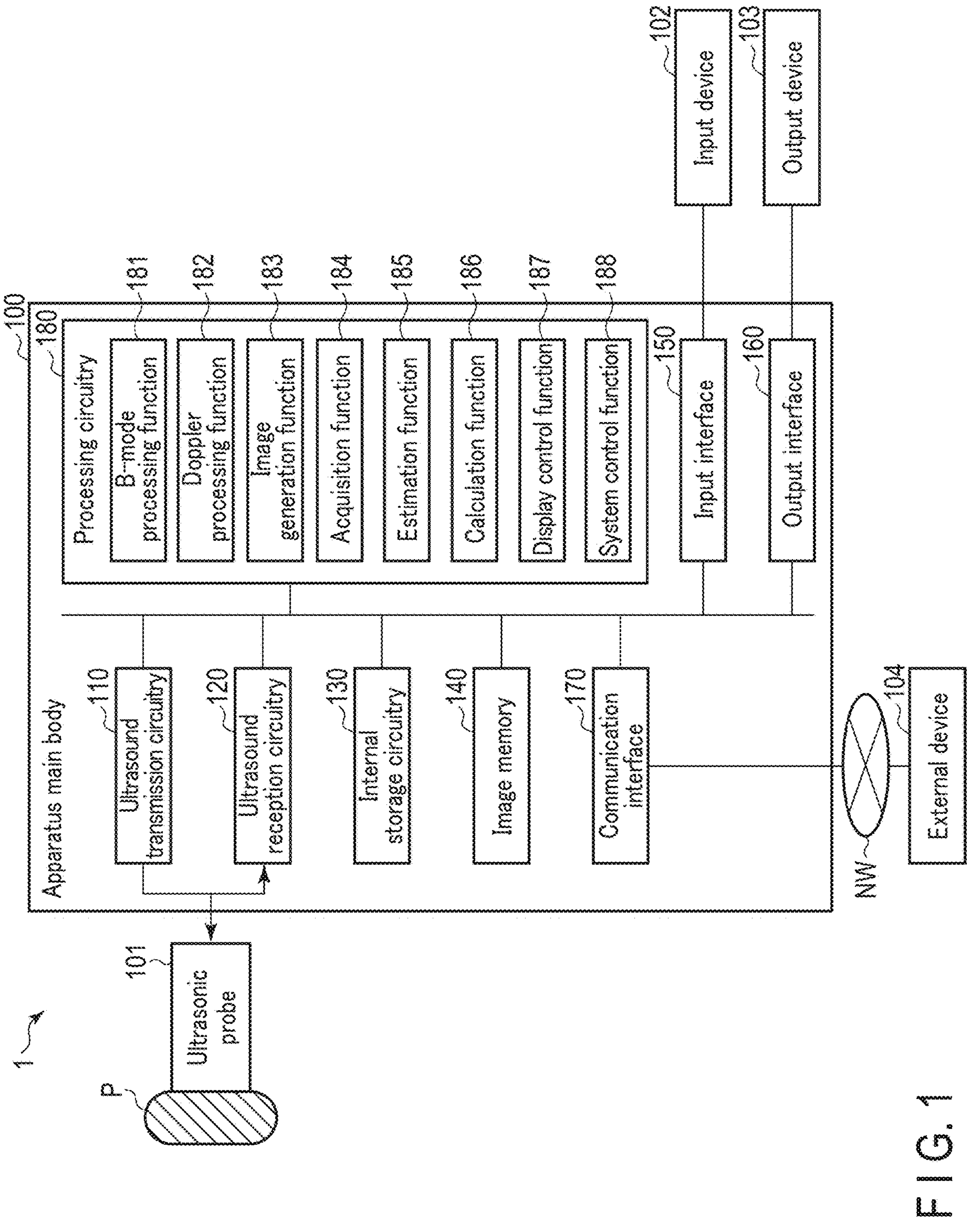
F I G. 1

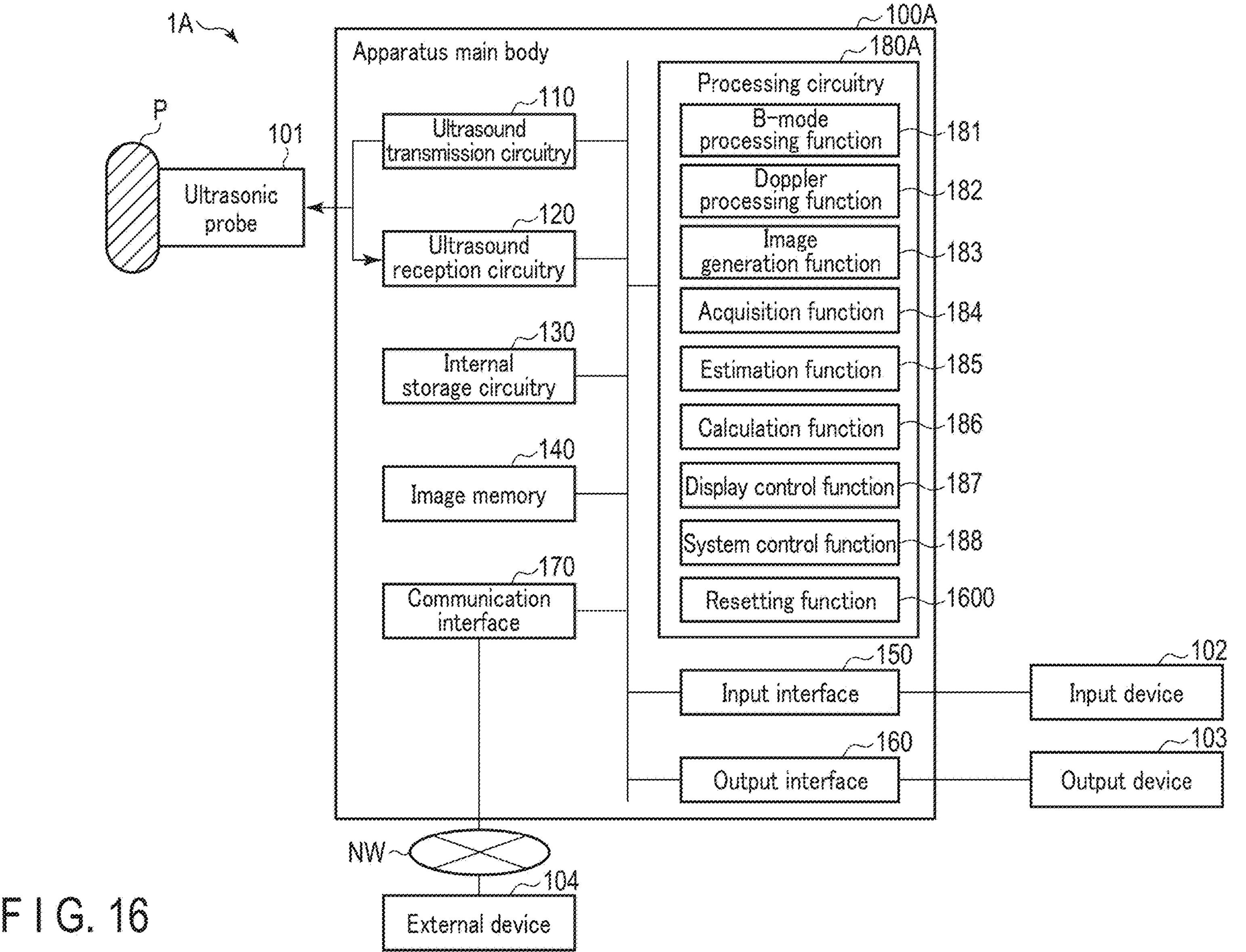
F I G. 16

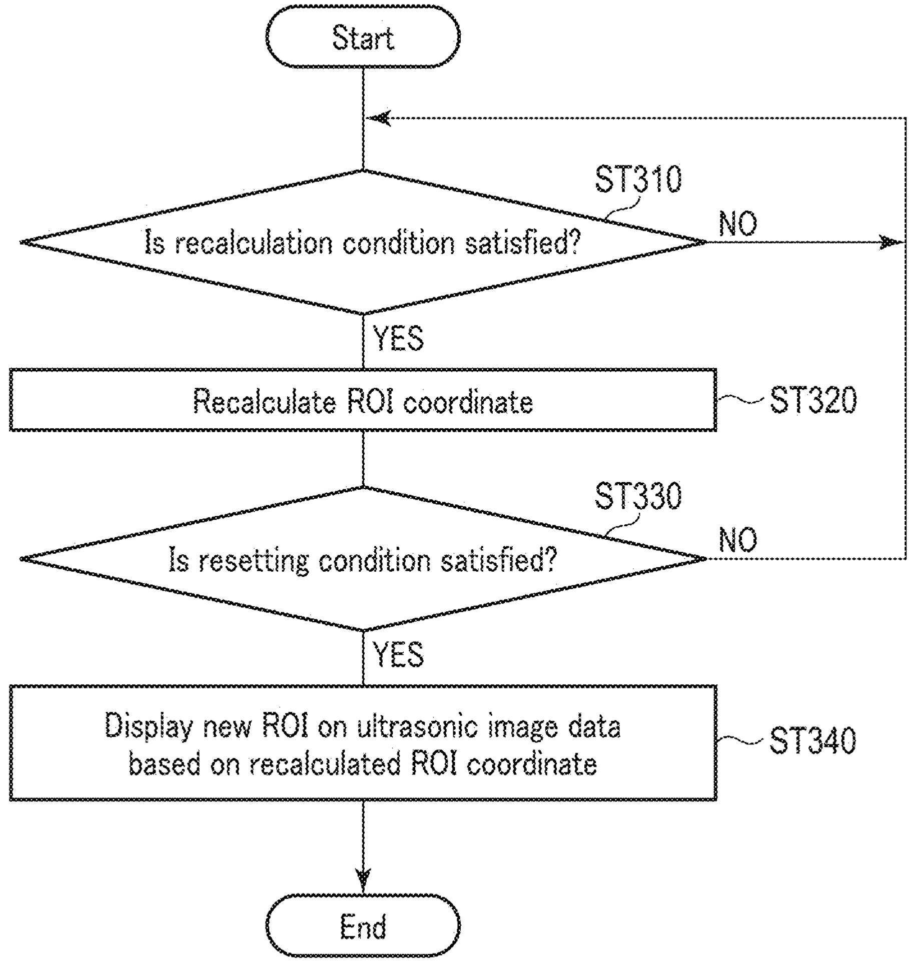
F I G. 17

ULTRASOUND DIAGNOSTIC APPARATUS

CROSS-REFERENCE TO RELATED APPLICATIONS

This application is based upon and claims the benefit of priority from Japanese Patent Applications No. 2021-064204, filed Apr. 5, 2021; and No. 2022-048858, filed Mar. 24, 2022; the entire contents of all of which are incorporated herein by reference.

FIELD

Embodiments described herein relate generally to an ultrasound diagnostic apparatus.

BACKGROUND

In recent years, some ultrasound diagnostic apparatuses equipped with a plurality of display modes have emerged. The plurality of display modes comprise of, for example, a B-mode of displaying on a screen a reflected echo signal of ultrasonic waves with brightness modulated, a bloodstream imaging mode of displaying a bloodstream in a two-dimensional image, and a shear wave elastography (SWE) mode of measuring the hardness of a biological tissue. These display modes differ from each other in respect of the size of a region of interest (ROI) including an examination target (such as tumor and lesion).

For example, in the case of the bloodstream imaging mode, it is preferable to set an ROI size covering an examination target and a peripheral region having an area larger than the area of the examination target. On the other hand, in the case of the SWE mode, it is preferable to set an ROI size simply covering an examination target.

As described above, since an optimal ROI size differs among types of display modes, a user needs to set an ROI every time the display mode is changed (transitioned). This not only burdens a user but may also prevent the setting of an optimal ROI.

BRIEF DESCRIPTION OF THE DRAWINGS

FIG. 1 is a block diagram showing a configuration example of an ultrasound diagnostic apparatus according to a first embodiment.

FIG. 16 is a block diagram showing a configuration example of an ultrasound diagnostic apparatus according to a third embodiment.

FIG. 17 is a flowchart showing a first specific example of a processing circuitry operation which executes the processing for resetting a region of interest of the third embodiment.

DETAILED DESCRIPTION

Figure 2:
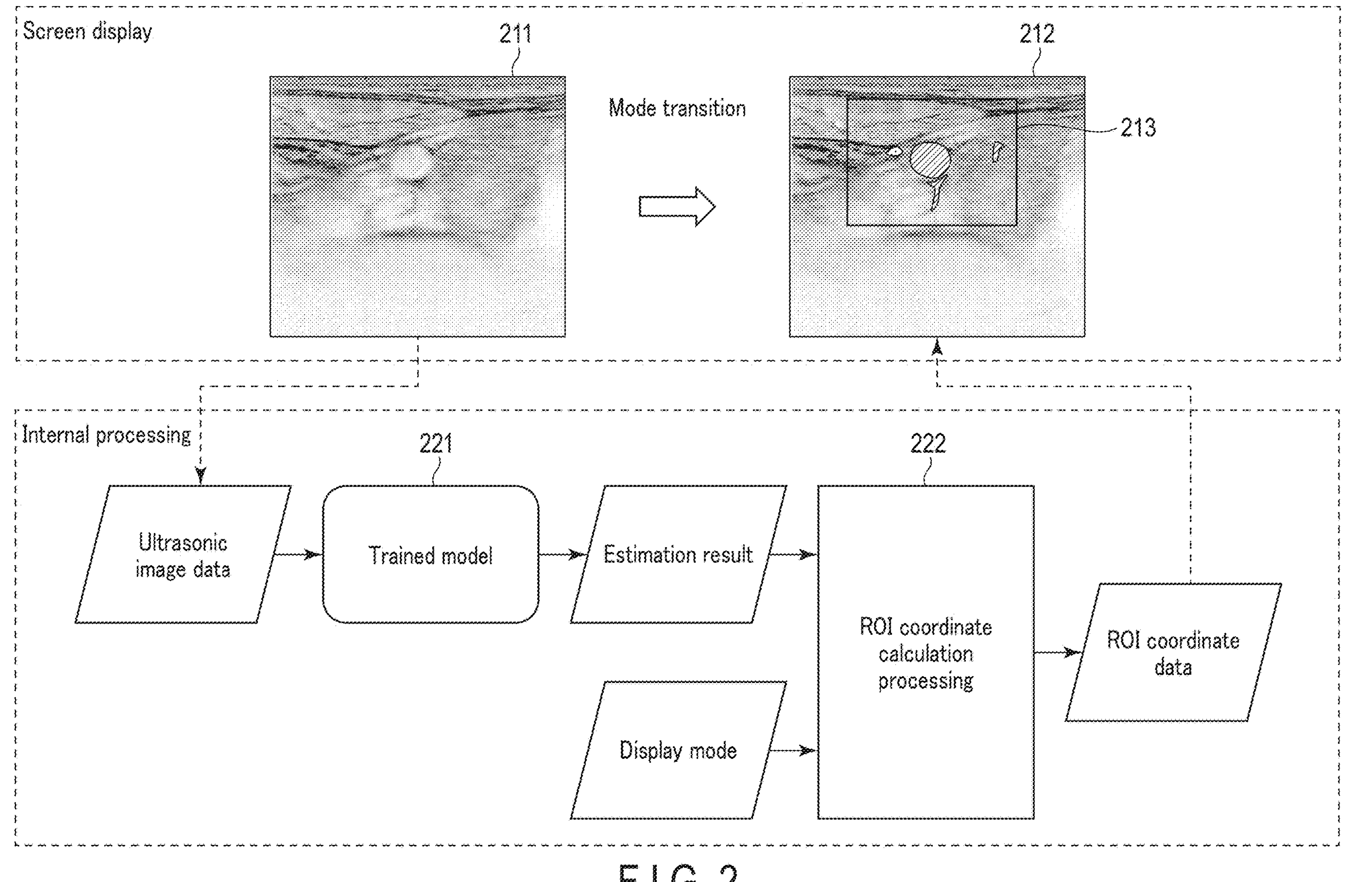
FIG. 2 is a diagram showing an example of screen display and internal processing related to the processing for automatically setting a region of interest of the first embodiment.

In general, according to one embodiment an ultrasound diagnostic apparatus includes processing circuitry. The processing circuitry acquires first ultrasonic image data of a first mode, estimates a position of an examination target included in the first ultrasonic image data by applying a trained model to the first ultrasonic image data and output an estimation result, calculates a coordinate of a region of interest corresponding to a second mode different from the first mode based on the estimation result and information on the second mode, and displays the region of interest on second ultrasonic image data of the second mode based on the coordinate.

Hereinafter, embodiments of an ultrasound diagnostic apparatus will be described in detail with reference to the accompanying drawings.

First Embodiment

FIG. 1 is a block diagram showing a configuration example of an ultrasound diagnostic apparatus according to a first embodiment. An ultrasound diagnostic apparatus 1 shown in FIG. 1 includes an apparatus main body 100 and an ultrasonic probe 101. The apparatus main body 100 is connected to an input device 102 and an output device 103. The apparatus main body 100 is also connected to an external device 104 via a network NW. The external device 104 is, for example, a server equipped with a picture archiving and communication system (PACS).

The ultrasonic probe 101, for example, executes ultrasound scanning in a scan area of a living body P, which is a subject, under the control of the apparatus main body 100. The ultrasonic probe 101 includes, for example, a plurality of piezoelectric vibrators, a matching layer provided between a case and the plurality of piezoelectric vibrators, and a backing material that prevents ultrasound waves from propagating backward with respect to a radiation direction from the piezoelectric vibrators. The ultrasonic probe 101 is, for example, a one-dimensional array linear probe in which a plurality of ultrasound transducers are arranged in a predetermined direction. The ultrasonic probe 101 is detachably connected to the apparatus main body 100. The ultrasonic probe 101 may be provided with buttons which are pressed when offset processing, an operation for freezing an ultrasonic image (freeze operation), and the like are performed.

The piezoelectric vibrators generate an ultrasound wave based on a drive signal supplied from ultrasound transmission circuitry 110 (described later) of the apparatus main body 100. An ultrasound wave is thereby transmitted from the ultrasonic probe 101 to the living body P. When an ultrasound wave is transmitted from the ultrasonic probe 101 to the living body P, the transmitted ultrasound wave is sequentially reflected by a discontinuous surface of the acoustic impedance of the body tissue of the living body P, and is received as a reflected wave signal by the plurality of piezoelectric vibrators. The amplitude of the received reflected wave signal depends on the difference in the acoustic impedance on the discontinuous surface from which the ultrasound wave is reflected. If the transmitted ultrasound pulse is reflected by a moving bloodstream or surface of a cardiac wall or the like, the frequency of the resultant reflected wave signal will be shifted, due to the Doppler effect, depending on the velocity component of the moving object in the ultrasonic transmission direction. The ultrasonic probe 101 receives the reflected wave signal from the living body P, and converts it into an electric signal.

FIG. 1 illustrates a connection relationship between a single ultrasonic probe 101 and the apparatus main body 100. However, the apparatus main body 100 can be connected to a plurality of ultrasonic probes. The connected ultrasonic probe to be used for the ultrasound scanning can be selected discretionarily by using, for example, a software button on a touch panel described later.

The apparatus main body 100 generates an ultrasonic image based on the reflected wave signal received by the ultrasonic probe 101. The apparatus main body 100 includes ultrasound transmission circuitry 110, ultrasound reception circuitry 120, internal storage circuitry 130, an image memory 140, an input interface 150, an output interface 160, a communication interface 170, and processing circuitry 180.

The ultrasound transmission circuitry 110 is a processor that supplies a drive signal to the ultrasonic probe 101. The ultrasound transmission circuitry 110 is implemented by, for example, trigger generation circuitry, delay circuitry, and pulser circuitry. The trigger generation circuitry repeatedly generates a rate pulse for forming a transmission ultrasound wave at a predetermined rate frequency. The delay circuitry gives each rate pulse generated by the trigger generation circuitry a delay time for each piezoelectric vibrator needed to converge the ultrasound waves generated from the ultrasonic probe into a beam and determine the transmission directivity. The pulser circuitry applies a drive signal (drive pulse) to the multiple ultrasound transducers of the ultrasonic probe 101 at a timing based on the rate pulse. The transmission direction from the surfaces of the piezoelectric vibrators can be discretionarily adjusted by varying the delay time given to each rate pulse through the delay circuitry.

The ultrasound transmission circuitry 110 can discretionarily change the output intensity of the ultrasound wave through a drive signal. In the ultrasound diagnostic apparatus, the influence of the attenuation of the ultrasound wave in the living body P can be reduced by increasing the output intensity. By reducing the influence of the attenuation of the ultrasound wave, the ultrasound diagnostic apparatus can obtain a reflected wave signal having a large S/N ratio when receiving the signal.

In general, when the ultrasound wave is propagated inside the living body P, the strength of the oscillation of the ultrasound wave corresponding to the output intensity (the strength is also referred to as "acoustic power") is attenuated. The attenuation of the acoustic power is caused by absorption, scattering, reflection, and the like. Also, the degree of acoustic power reduction depends on the frequency of the ultrasound wave and the distance of the ultrasound wave in the radiation direction. For example, the degree of attenuation is increased by increasing the frequency of the ultrasound wave. Also, the longer the distance of the ultrasound wave in the radiation direction, the larger the degree of attenuation.

The ultrasound reception circuitry 120 is a processor that performs various types of processing on the reflected wave signal received by the ultrasonic probe 101, and thereby generates a reception signal. The ultrasound reception circuitry 120 generates a reception signal for the reflected wave signal of the ultrasound wave obtained by the ultrasonic probe 101. Specifically, the ultrasound reception circuitry 120 is implemented by, for example, a preamplifier, an A/D converter, a demodulator, and a beam former. The preamplifier performs gain correction processing by amplifying the reflected wave signal received by the ultrasonic probe 101 for each channel. The A/D converter converts the gain-corrected reflected wave signal into a digital signal. The demodulator demodulates the digital signal. The beam former, for example, provides the demodulated digital signal with a delay time needed to determine the reception directivity, and adds a plurality of digital signals provided with the delay time. Through the addition processing by the beam former, a reception signal with an enhanced reflection component in a direction corresponding to the reception directivity is generated.

The internal storage circuitry 130 includes, for example, a magnetic storage medium, an optical storage medium, or a processor-readable storage medium such as a semiconductor memory. The internal storage circuitry 130 stores a program for implementing ultrasound transmission-reception, a program related to the processing of automatically setting a region of interest described later, various data, and the like. The programs and various data may be pre-stored in, for example, the internal storage circuitry 130. Alternatively, the programs and various data may be stored and distributed in, for example, a non-transitory storage medium, then read from the non-transitory storage medium and installed in the internal storage circuitry 130. The internal storage circuitry 130 stores B-mode image data, contrast image data, image data related to a bloodstream image, and the like that are generated at the processing circuitry 180, in accordance with an operation input via the input interface 150. The internal storage circuitry 130 can also transfer the stored image data to the external device 104 or the like via the communication interface 170.

The internal storage circuitry 130 may be a drive or the like which reads and writes various types of information to and from a portable storage medium, such as a CD drive, a DVD drive, and a flash memory. The internal storage circuitry 130 can also write the stored data onto a portable storage medium and store the data in the external device 104 through the portable storage medium.

The image memory 140 includes, for example, a magnetic storage medium, an optical storage medium, or a processor-readable storage medium such as a semiconductor memory. The image memory 140 stores image data corresponding to a plurality of frames immediately before a freeze operation input via the input interface 150. The image data stored in the image memory 140 is, for example, continuously displayed (cine-displayed).

The internal storage circuitry 130 and the image memory 140 need not necessarily be implemented by independent storage devices. The internal storage circuitry 130 and the image memory 140 may be implemented by a single storage device. Each of the internal storage circuitry 130 and the image memory 140 may be implemented by a plurality of storage devices.

The input interface 150 receives various commands from an operator through the input device 102. The input device 102 is, for example, a mouse, a keyboard, a panel switch, a slider switch, a trackball, a rotary encoder, an operation panel, or a touch panel. The input interface 150 is connected to the processing circuitry 180 via a bus, for example, thereby converting an operation command input by the operator, into an electric signal, and outputting the electric signal to the processing circuitry 180. The input interface 150 is not limited to a component connected to a physical operation component such as a mouse and keyboard. Examples of the input interface also include circuitry configured to receive an electric signal corresponding to an operation command input from an external input device provided separately from the ultrasound diagnostic apparatus 1 and to output the electric signal to the processing circuitry 180.

The output interface 160 is an interface for outputting, for example, an electric signal from the processing circuitry 180 to the output device 103. The output device 103 is any display such as a liquid crystal display, an organic EL display, an LED display, a plasma display, or a CRT display. The output device 103 may be a touch panel display doubling as the input device 102. The output device 103 may further include a speaker that outputs voice in addition to a display. The output interface 160 is connected to the processing circuitry 180 via a bus, for example, and outputs an electric signal from the processing circuitry 180 to the output device 103.

The communication interface 170 is connected to the external device 104 via, for example, the network NW so that it performs data communication with the external device 104.

The processing circuitry 180 is, for example, a processor that functions as the center of the ultrasound diagnostic apparatus 1. The processing circuitry 180 executes a program stored in the internal storage circuitry 130, thereby implementing a function corresponding to the program. The processing circuitry 180 includes, for example, a B-mode processing function 181, a Doppler processing function 182, an image generation function 183, an acquisition function 184 (acquisition unit), an estimation function 185 (estimation unit), a calculation function 186 (calculation unit), a display control function 187 (display controller), and a system control function 188.

The B-mode processing function 181 is a function for generating B-mode data based on the reception signal received from the ultrasound reception circuitry 120. With the B-mode processing function 181, the processing circuitry 180 performs, for example, envelope detection processing, logarithmic compression processing, and the like on the reception signal received from the ultrasound reception circuitry 120 to generate data (B-mode data) that expresses a signal intensity by brightness. The generated B-mode data is stored in a raw data memory (not shown) as B-mode raw data on a two-dimensional ultrasonic scanning line (raster).

Further, with the B-mode processing function 181, the processing circuitry 180 can execute a contrast echo method such as contrast harmonic imaging (CHI). Specifically, the processing circuitry 180 can separate reflection wave data (a harmonic component or a subharmonic component) of the living body P injected with a contrast agent, and reflection wave data (a fundamental wave component) whose reflection source is a tissue in the living body P. As a result, the processing circuitry 180 can extract a harmonic component or a subharmonic component from the reflection wave data of the living body P, to generate B-mode data for generating contrast image data.

The B-mode data for generating contrast image data is data expressing a signal intensity of the reflection wave, whose reflection source is a contrast agent, by brightness. The processing circuitry 180 can extract a fundamental wave component from the reflection wave data of the living body P, to generate B-mode data for generating tissue image data.

When performing the CHI, the processing circuitry 180 can extract a harmonic component by a method different from the above-described method that uses a filtering process. In the harmonic imaging, an amplitude modulation (AM) method, a phase modulation (PM) method, or an imaging method called an AMPM method, which is a combination of the AM method and the PM method, is performed.

In the AM method, the PM method, and the AMPM method, ultrasound transmission is performed more than once for a single scanning line, with different amplitudes and/or phases. Through the above processing, the ultrasound reception circuitry 120 generates a plurality of reflection wave data at each scanning line, and outputs the generated reflection wave data. With the B-mode processing function 181, the processing circuitry 180 performs addition/subtraction processing on the plurality of reflection wave data at the respective scanning lines in accordance with a modulation method, thereby extracting a harmonic component. Then, the processing circuitry 180 performs envelope detection processing or the like on the reflection wave data of the harmonic component, thereby generating B-mode data.

The Doppler processing function 182 is a function of analyzing the frequency of the reception signal received from the ultrasound reception circuitry 120 and thereby generating data (Doppler information) obtained by extracting motion information based on the Doppler effect of a moving object in a region of interest (ROI) set in the scan area. The generated Doppler information is stored in a raw data memory (not shown) as Doppler raw data (also referred to as "Doppler data") on a two-dimensional ultrasonic scanning line.

Specifically, with the Doppler processing function 182, the processing circuitry 180 estimates an average velocity, an average dispersion value, an average power value, etc., for example, as motion information of a moving object at each sampling point, and generates Doppler data indicating the estimated motion information. The moving object is, for example, a bloodstream, tissue of a cardiac wall, etc., and a contrast agent. With the Doppler processing function 182, the processing circuitry 180 according to the present embodiment estimates an average bloodstream velocity, a dispersion value of a bloodstream velocity, a power value of a bloodstream signal, etc., as motion information of a bloodstream (bloodstream information) at each sampling point, and generates Doppler data indicating the estimated bloodstream information.

Furthermore, with the Doppler processing function 182, the processing circuitry 180 can perform a color Doppler method also called a color flow mapping (CFM) method. In the CFM method, the transmission and reception of ultrasound waves are performed on multiple scanning lines more than once. In the CFM method, a moving target indicator (MTI) filter is applied to data strings in the same position, for example, to thereby suppress signals (clutter signals) related to stationary tissue or slow-moving tissue so that bloodstream-related signals are extracted. In the CFM method, the extracted bloodstream signals are used to estimate the bloodstream information such as a bloodstream velocity, bloodstream dispersion, and bloodstream power. With the image generation function 183 described later, a distribution of the estimated bloodstream information is generated, for example, as ultrasonic image data (color Doppler image data) displayed in color in two dimensions. Hereinafter, a mode of the ultrasound diagnostic apparatus that extracts a bloodstream signal through an MTI filter based on the Doppler method and uses the extracted bloodstream signal for imaging will be referred to as a "bloodstream imaging mode". Color display refers to displaying the distribution of the bloodstream information in accordance with a predetermined color code, and includes gray-scale display.

The bloodstream imaging mode includes various types in accordance with desired clinical information. In general, there is a bloodstream imaging mode for velocity display that allows for visualization of a bloodstream direction or an average bloodstream velocity, and a bloodstream imaging mode for power display that allows for visualization of bloodstream signal power.

The bloodstream imaging mode for velocity display is a mode of displaying color corresponding to the Doppler shift frequency based on a bloodstream direction or average bloodstream velocity. For example, the bloodstream imaging mode for velocity display represents, as a flow direction, an oncoming flow by a red-based color and a receding flow by a blue-based color, thereby representing the velocity difference between the oncoming flow and the receding flow through the difference in the hue. The bloodstream imaging mode for velocity display may also be called a "color Doppler mode" or a "color Doppler imaging (CDI) mode".

The bloodstream imaging mode for power display is a mode of representing bloodstream signal power by, for example, a red-based color phase, brightness of the color, or a change in chromaticness. The bloodstream imaging mode for power display may also be called a "power Doppler (PD) mode". Since the bloodstream imaging mode for power display can represent a bloodstream at high sensitivity, as compared to the bloodstream imaging mode for velocity display, the bloodstream imaging mode for power display may be called a "high-sensitivity bloodstream imaging mode".

In addition to the CDI mode and the PD mode, the bloodstream imaging mode includes a bloodstream imaging mode for low flow rate (SMI: Superb Micro-vascular Imaging) specialized in representing a low flow rate, a high-resolution bloodstream imaging mode (ADF: Advanced Dynami Flow), and the like. These bloodstream imaging modes have different imaging systems defined by a scan protocol, signal processing, and the like. The bloodstream imaging mode may include modes other those listed above.

The image generation function 183 is a function of generating B-mode image data based on the data generated by the B-mode processing function 181. With the image generation function 183, the processing circuitry 180, for example, converts (scan-converts) a scanning line signal sequence of an ultrasonic scan into a scanning line signal sequence of a video format representatively used by television, etc., to generate image data for display (display image data). Specifically, the processing circuitry 180 executes a raw-pixel conversion, such as a coordinate conversion corresponding to the mode of the ultrasonic scan by the ultrasonic probe 101, on B-mode raw data stored in the raw data memory to generate two-dimensional B-mode image data (also referred to as "ultrasonic image data") consisting of pixels. In other words, with the image generation function 183, the processing circuitry 180 generates a plurality of ultrasonic images (medical images) respectively corresponding to a plurality of consecutive frames by transmission and reception of ultrasound waves.

The processing circuitry 180 also executes, for example, a raw-pixel conversion on Doppler raw data stored in the raw data memory to generate Doppler image data that visualizes bloodstream information. The Doppler image data is average velocity image data, dispersion image data, power image data, or image data of a combination thereof. The processing circuitry 180 generates, as Doppler image data, color Doppler image data that represents the bloodstream information by color, and Doppler image data that represents a piece of bloodstream information in a waveform shape with a gray scale. The color Doppler image data is generated when the above-described bloodstream imaging mode is executed.

The acquisition function 184 is a function of acquiring various data related to the processing of automatically setting a region of interest described later. Specifically, with the acquisition function 184, the processing circuitry 180, for example, acquires an instruction for executing another display mode different from the current display mode. The processing circuitry 180 also acquires ultrasonic image data in the current display mode upon acquisition of the instruction for execution. The "instruction for execution" may be rephrased as information related to another display mode ("display mode information") or information related to a display mode after transition ("transition mode information").

The estimation function 185 is a function of estimating the position of an examination target included in ultrasonic image data by applying a trained model to the ultrasonic image data. Specifically, with the estimation function 185, the processing circuitry 180, for example, estimates the position of an examination target included in ultrasonic image data by applying a trained model to the ultrasonic image data, and outputs an estimation result. As an example of estimating the position of an examination target, when a region in the ultrasonic image data exists in which the likelihood is equal to or greater than a threshold, it is estimated that an examination target is included in that region. In this case, the result of estimation includes, for example, at least one region estimated to include an examination target (this region may be referred to as a "detection region" or a "unit of detection"). When the estimation likelihood of all the regions in the ultrasonic image data does not exceed (or fall below) a threshold, it is estimated that the image data does not include an examination target. In this case, the estimation result does not include information on a unit of detection, and may include, for example, information indicating that no examination target is detected.

Namely, the processing circuitry 180 outputs the estimation result regardless of whether the position of an examination target is estimated or not, in other words, regardless of whether a unit of detection is included or not.

The aforementioned trained model is, for example, a prepared machine learning model trained based on ultrasonic image data including an examination target. Machine learning may be performed either for each of the segmented regions obtained by dividing the ultrasonic image data into arbitrary regions, or for each of the regions combining the segmented regions. In this case, the estimation function 185 likewise performs estimation processing for each of the segmented regions obtained by dividing the ultrasonic image data into arbitrary regions.

The machine learning model according to the present embodiment is assumed, typically, as a deep neural network (DNN), which is a multiple-layer network model simulating the neural circuitry of the brain of a living being. The DNN includes a composite function with parameters that are defined by a combination of a plurality of adjustable functions and parameters.

The calculation function 186 is a function for calculating a coordinate of a region of interest (hereinafter referred to as a "ROI coordinate") corresponding to a desired display mode based on the estimation result. The "ROI coordinate" of the present embodiment includes the position and the size of the ROI. Specifically, with the calculation function 186, the processing circuitry 180, for example, specifies one or more detection areas from one or more units of detection included in the estimation result. The processing circuitry 180 then selects a most probable detection area from among the one or more detection areas and calculates a ROI coordinate including at least the detection area. At this time, the calculation of the ROI coordinate is performed according to a desired display mode. The detection area is an entire region where one or more units of detection overlap. Detailed descriptions will be given later.

If the estimation result does not include an examination target, the processing circuitry 180 need not perform the processing of the calculation function 186. In this case, a user manually sets the position and the size of the ROI as is conventionally done.

The display control function 187 is a function of causing a display as the output device 103 to display an image based on various kinds of ultrasonic image data generated by the image generation function 183. Specifically, with the display control function 187, the processing circuitry 180, for example, controls the displaying, on the display, of an image based on the B-mode image data, the Doppler image data, or the image data including both of these types of data, generated by the image generation function 183.

More specifically, with the display control function 187, the processing circuitry 180 converts (scan-converts) a scanning line signal sequence of an ultrasonic scan into a scanning line signal sequence of a video format representatively used by television, etc., to generate display image data. The processing circuitry 180 may also perform various types of processing, such as dynamic range, brightness, contrast, γ curve corrections, and an RGB conversion, on the display image data. The processing circuitry 180 may also add supplementary information, such as textual information of various parameters, a scale, or a body mark, to the display image data. The processing circuitry 180 may also generate a user interface (graphical user interface (GUI)) to allow the operator to input various commands through the input device, and cause the display to display the GUI.

With the display control function 187, the processing circuitry 180 displays a ROI on the ultrasonic image data based on a ROI coordinate calculated by the calculation function 186. The processing circuitry 180 may display information related to the automatic setting of the ROI. Specifically, the processing circuitry 180 changes the display of a letter or a mark notifying a user of completion of automatic setting of an ROI after the transition of a display mode, or changes a display color of an ROI in the display mode post-transition. With regard to the change of a display color, for example, a display color of an automatically set ROI may be changed from a conventional display color; alternately, a default display color of a ROI displayed when no ROI has been automatically set may be changed from a conventional display color.

The system control function 188 is a function of integrally controlling the overall operations of the ultrasound diagnostic apparatus 1. For example, with the system control function 188, the processing circuitry 180 controls the ultrasound transmission circuitry 110 and the ultrasound reception circuitry 120 based on a parameter related to transmission and reception of ultrasound waves.

The processing circuitry 180 may perform an imaging mode other than the B-mode and the bloodstream imaging mode. The imaging mode other than the B-mode and the bloodstream imaging mode includes, for example, a strain elastography mode, a shear wave elastography (SWE) mode, and an attenuation imaging (ATI) mode.

A configuration of the ultrasound diagnostic apparatus according to the first embodiment has been described above. Next, an overview of the processing according to the first embodiment will be described with reference to FIG. 2.

FIG. 2 is a diagram showing an example of screen display and internal processing related to the processing of automatically setting a region of interest of the first embodiment. FIG. 2 shows, as a display screen, an ultrasonic image 211 and an ultrasonic image 212 differing in the display mode before and after mode transition. FIG. 2 illustrates internal processing (processing of automatically setting a region of interest) performed during mode transition.

The screen display will be described first. The ultrasound diagnostic apparatus 1 according to the first embodiment changes the screen display from the ultrasonic image 211 to the ultrasonic image 212 in response to an operation related to mode transition performed by a user. The ultrasonic image 211 corresponds to the current display mode (which may be referred to as "a first mode", "a first display mode", and "a display mode before transition"). The ultrasonic image 212 corresponds to a display mode post-transition (which may be referred to as "a second mode" and "a second display mode"). A ROI 213 optimal to the display mode after transition is also displayed in the ultrasonic image 212. The state during mode transition may be a state in which a screen update of the ultrasonic image 211 is stopped, that is, a state that is approximately the same as a freeze state.

The internal processing will be described next. With the acquisition function 184, the processing circuitry 180, for example, acquires ultrasonic image data and information related to the display mode after transition, in response to an operation related to mode transition performed by a user. With the estimation function 185, the processing circuitry 180 applies a trained model 221 to the ultrasonic image data and generates an estimation result concerning the ultrasonic image data. With the calculation function 186, the processing circuitry 180 executes ROI coordinate calculation processing 222 and calculates a ROI coordinate corresponding to the display mode after transition based on the estimation result and the information on the display mode post-transition.

Figure 3:
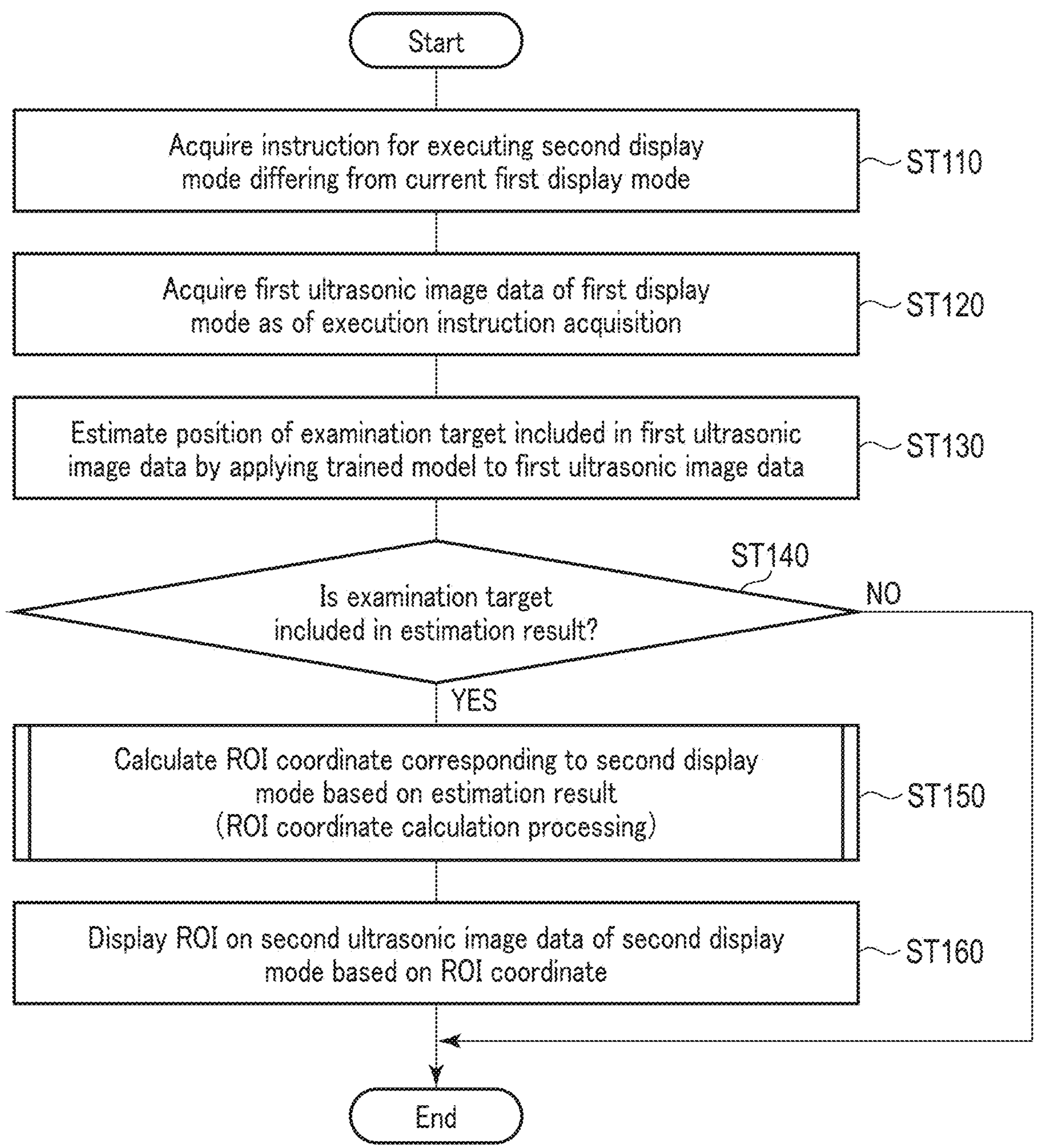
FIG. 3 is a flowchart showing an example of an operation of processing circuitry which executes the processing for automatically setting a region of interest of the first embodiment.

FIG. 3 is a flowchart showing an example of an operation of the processing circuitry which executes the processing of automatically setting a region of interest of the first embodiment. The processing of automatically setting a region of interest shown in FIG. 3 is started, for example, in response to an operation related to mode transition performed by a user. The operation related to mode transition is, for example, an operation of executing a display mode different from the current display mode.

(Step ST110)

When the processing of automatically setting a region of interest starts, the processing circuitry 180 executes the acquisition function 184. When the processing circuitry 180 executes the acquisition function 184, the processing circuitry 180 acquires an instruction for executing a second display mode input by a user and differing from the current first display mode. In the descriptions provided hereinafter, the first display mode is the B-mode, and the second display mode is the bloodstream imaging mode.

(Step ST120)

After acquiring the execution instruction from the user, the processing circuitry 180 further acquires first ultrasonic image data of the first display mode upon the acquisition of the execution instruction. The first ultrasonic image data acquired may be video data including two or more frames.

(Step ST130)

After acquiring the first ultrasonic image data, the processing circuitry 180 executes the estimation function 185. When the processing circuitry 180 executes the estimation function 185, the processing circuitry 180 estimates the position of an examination target included in the first ultrasonic image data by applying a trained model to the first ultrasonic image data, and outputs an estimation result. Specifically, the processing circuitry 180 generates an estimation result including one or more units of detection by applying a trained model to the first ultrasonic image data. If the estimation result does not include an examination target, it is determined that the estimation result does not include a unit of detection.

(Step ST140)

After generating the estimation result, the processing circuitry 180 determines whether or not the estimation result includes an examination target. In other words, the processing circuitry 180 determines whether or not the estimation result includes information on a unit of detection. If the estimation result includes information on a unit of detection, the processing proceeds to step ST150. If the estimation result does not include information on a unit of detection, the processing is ended.

(Step ST150)

After it is determined that the estimation result includes information on a unit of detection, the processing circuitry 180 executes the calculation function 186. When the processing circuitry 180 executes the calculation function 186, the processing circuitry 180 calculates a ROI coordinate corresponding to the second display mode based on the estimation result (the information on a unit of detection). Hereinafter, the processing of step ST150 will be referred to as "ROI coordinate calculation processing". A specific example of the ROI coordinate calculation processing will be described using the flowchart shown in FIG. 4.

Figure 4:
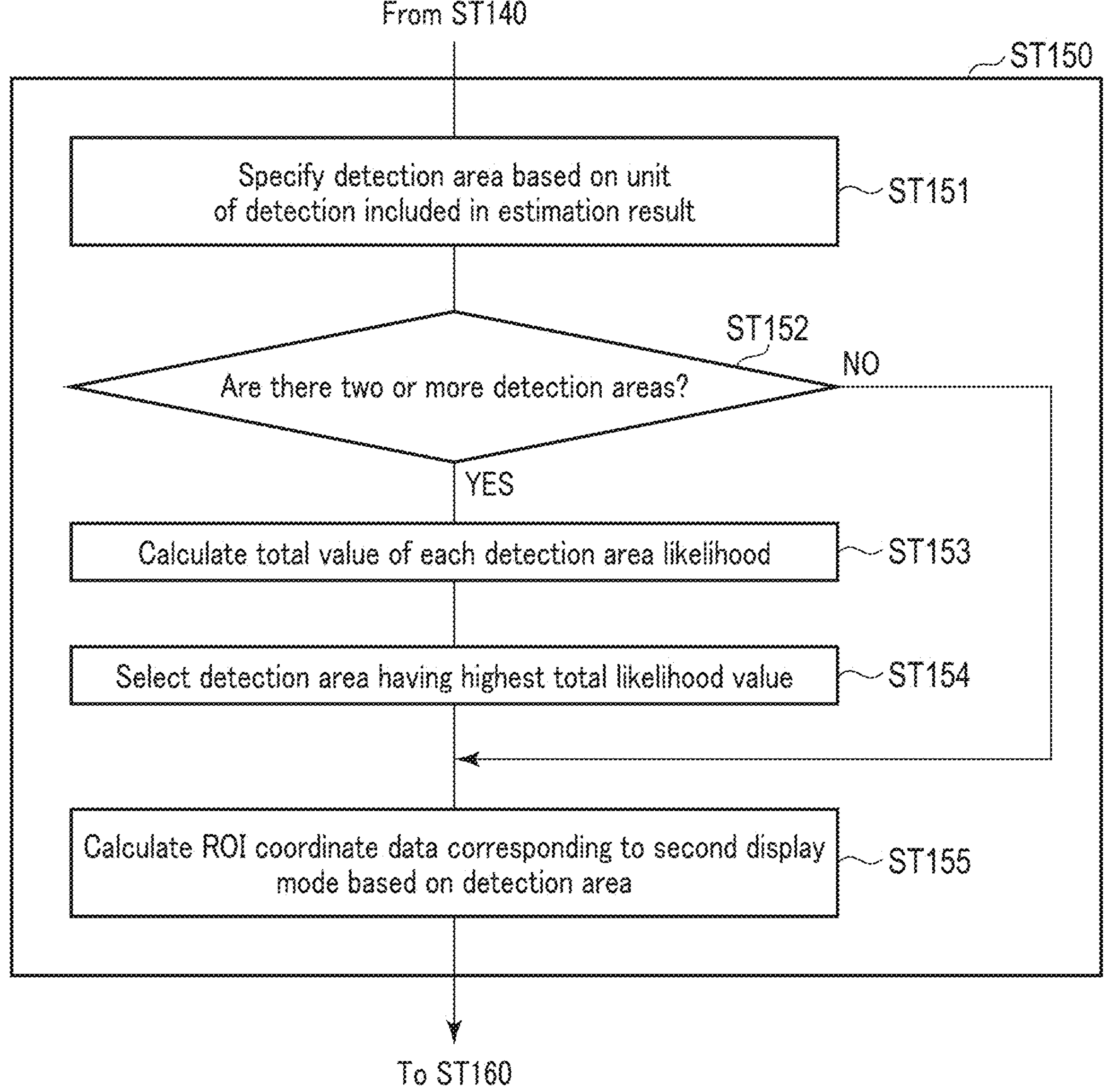
FIG. 4 is a flowchart showing an example of ROI coordinate calculation processing in the flowchart shown in FIG. 3.

FIG. 4 is a flowchart showing an example of the ROI coordinate calculation processing in the flowchart shown in FIG. 3. The flowchart shown in FIG. 4 transitions from step ST140 shown in FIG. 3.

(Step ST151)

After it is determined that the estimation result includes information on a unit of detection, the processing circuitry 180 specifies a detection area based on the unit of detection included in the estimation result. Specifically, the processing circuitry 180 specifies one or more detection areas from one or more units of detection. The specification of a detection area will be described in detail below. "Specifying one or more detection areas from one or more units of detection" includes, for example, any one of: specifying a single detection area from a single unit of detection, specifying a single detection area from multiple units of detection, and specifying multiple detection areas from multiple units of detection. Each of the cases will be described below with reference to FIGS. 5 to 7.

Figure 5:
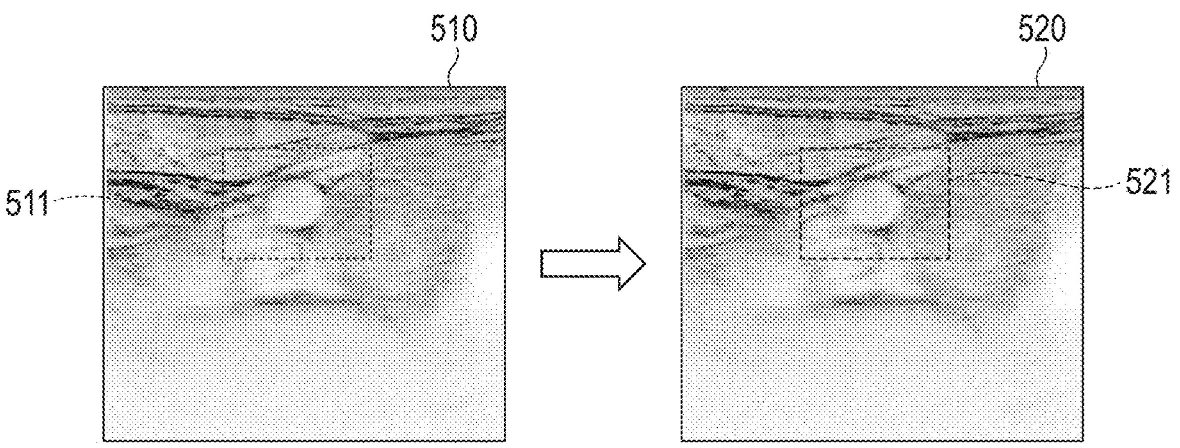
FIG. 5 is a diagram illustrating the specification of a single detection area from a single unit of detection.

FIG. 5 is a diagram illustrating the specification of a single detection area from a single unit of detection. FIG. 5 shows an ultrasonic image 510 and an ultrasonic image 520 before and after specifying the detection area. The ultrasonic image 510 includes a single unit 511 of detection. Thus, the processing circuitry 180 specifies a single unit 511 of detection as a detection area. As a result, the ultrasonic image 520 shows the specified single detection area 521. In other words, the detection area 521 is configured by a single unit 511 of detection.

Figure 6:
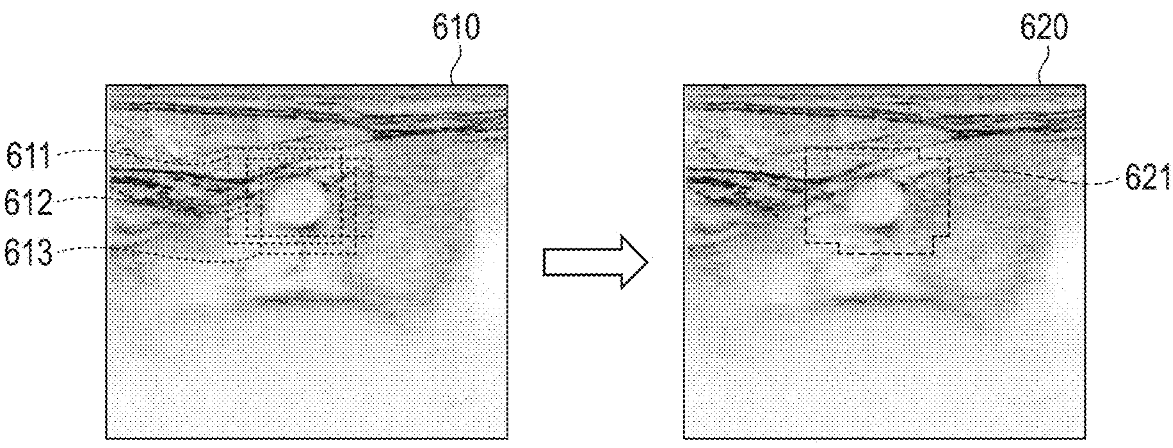
FIG. 6 is a diagram illustrating the specification of a single detection area from multiple units of detection.

FIG. 6 is a diagram illustrating the specification of a single detection area from multiple units of detection. FIG. 6 shows an ultrasonic image 610 and an ultrasonic image 620 before and after specifying the detection area. The ultrasonic image 610 includes multiple units 611 to 613 of detection. The multiple units 611 to 613 of detection partially overlap each other. Therefore, the processing circuitry 180 specifies, as a detection area, a contour including the multiple units 611 to 613 of detection. As a result, the ultrasonic image 620 shows the specified single detection area 621. In other words, the detection area 621 is configured by multiple units 611, 612, and 613 of detection.

Figure 7:
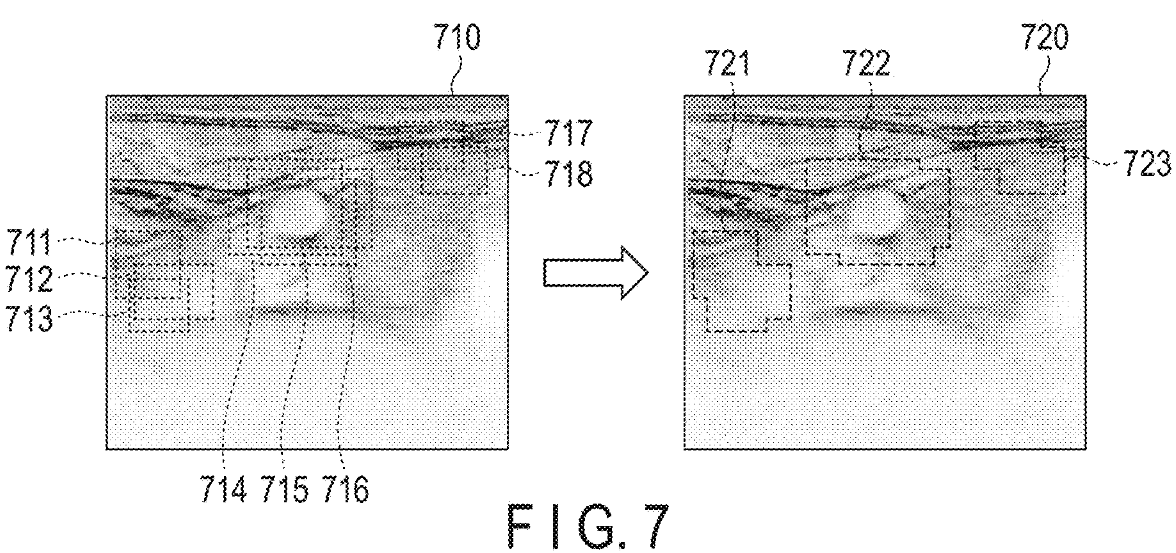
FIG. 7 is a diagram illustrating the specification of multiple detection areas from multiple units of detection.

FIG. 7 is a diagram illustrating the specification of multiple detection areas from multiple units of detection. FIG. 7 shows an ultrasonic image 710 and an ultrasonic image 720 before and after specifying the detection area. The ultrasonic image 710 includes multiple units 711 to 718 of detection. The multiple units 711 to 713 of detection, the multiple units 714 to 716 of detection, and the multiple units 717 and 718 of detection, respectively, partially overlap each other. Therefore, the processing circuitry 180 specifies, as a detection area, each of a contour including the multiple units 711 to 713 of detection, a contour including the multiple units 714 to 716 of detection, and a contour including the multiple units 717 and 718 of detection. As a result, the ultrasonic image 720 shows the specified multiple detection areas 721 to 723. In other words, the detection area 721 is configured by the multiple units 711, 712, and 713 of detection, the detection area 722 is configured by the multiple units 714, 715, and 716 of detection, and the detection area 723 is configured by the multiple units 717 and 718 of detection.

(Step ST152)

After specifying one or more detection areas, the processing circuitry 180 determines whether or not the number of detection areas is two or more. If the number of detection areas is two or more, the processing proceeds to step ST153. If the number of detection areas is not two or more, (i.e., one), the processing proceeds to step ST155.

(Step ST153)

After determining that the number of detection areas is two or more, the processing circuitry 180 calculates a total likelihood value of each detection area.

(Step ST154)

After calculating a total likelihood value of each detection area, the processing circuitry 180 selects a detection area having the highest total value of likelihood. A specific example of the processing of step ST153 and step ST154 will be described below with reference to FIG. 8.

Figure 8:
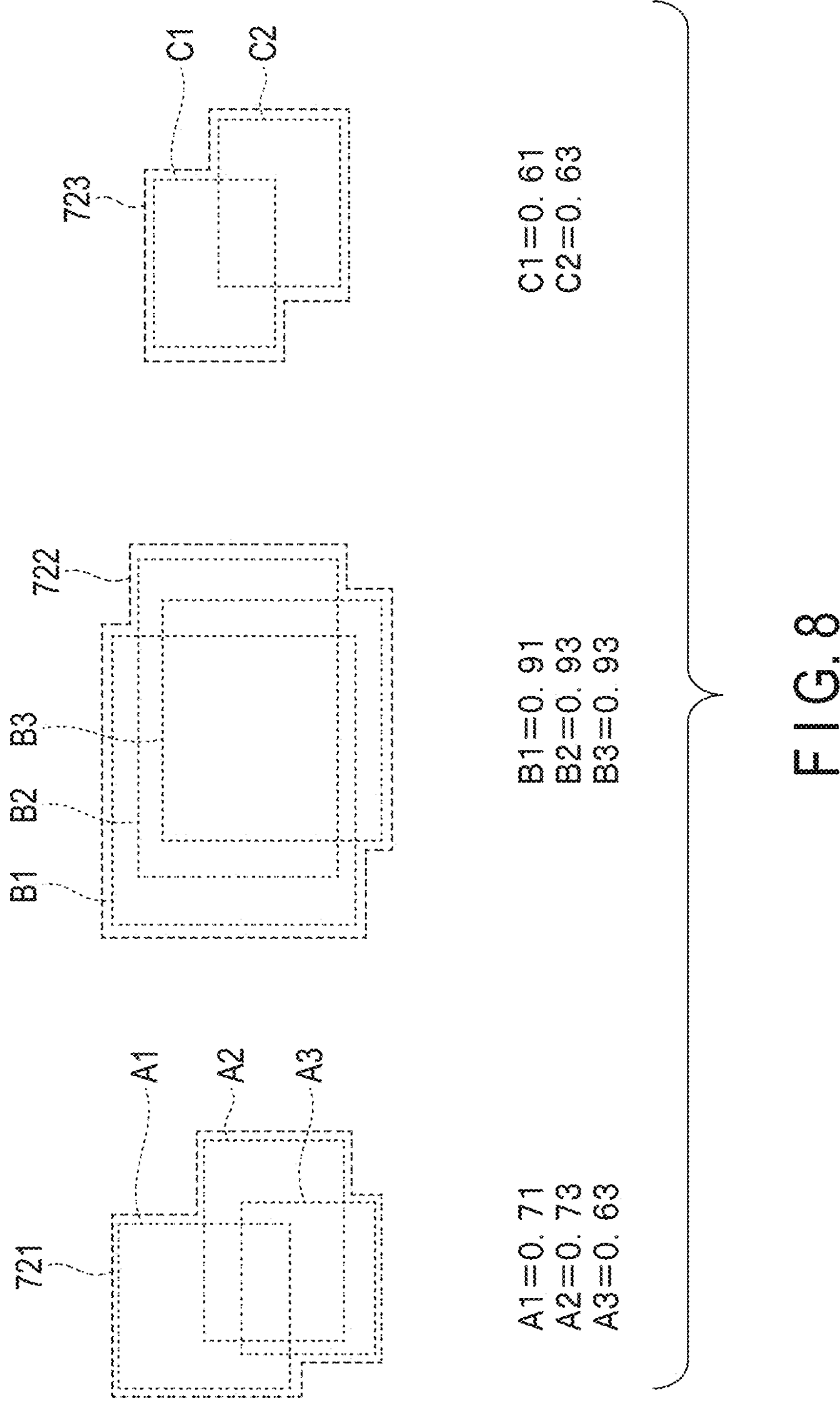
FIG. 8 is a diagram illustrating an example of the likelihood of the units of detection included in the multiple detection areas.

FIG. 8 is a diagram illustrating an example of the likelihood of the units of detection included in the multiple detection areas. FIG. 8 shows the detection area 721, the detection area 722, and the detection area 723 corresponding to the multiple detection areas included in the ultrasonic image 720 shown in FIG. 7. The detection area 721 shows multiple units A1, A2, and A3 of detection corresponding to the multiple units 711, 712, and 713 of detection. Likewise, the detection area 722 shows multiple units B1, B2, and B3 of detection corresponding to the multiple units 714, 715, and 716 of detection, and the detection area 723 shows multiple units C1 and C2 of detection corresponding to the multiple units 717 and 718 of detection.

For the detection area 721, the processing circuitry 180 calculates a total value "2.07" combining the likelihood "0.71" of the unit A1 of detection, the likelihood "0.73" of the unit A2 of detection, and the likelihood "0.63" of the unit A3 of detection. For the detection area 722, the processing circuitry 180 calculates a total value "2.77" combining the likelihood "0.91" of the unit B1 of detection, the likelihood "0.93" of the unit B2 of detection, and the likelihood "0.93" of the unit B3 of detection. Likewise, for the detection area 723, the processing circuitry 180 calculates a total value "1.24" combining the likelihood "0.61" of the unit C1 of detection and the likelihood "0.63" of the unit C2 of detection. After calculating a total likelihood value of each detection area, the processing circuitry 180 selects the detection area 722 having the highest likelihood total value.

(Step ST155)

After determining that the number of detection areas is one in step ST152 or after selecting a detection area in step ST154, the processing circuitry 180 calculates ROI coordinate data corresponding to the second display mode based on the detection area. In other words, the processing circuitry 180 calculates ROI coordinate data corresponding to the second display mode based on the estimation result and the information on the second display mode. A specific example of step ST155 will be described below with reference to FIG. 9.

Figure 9:
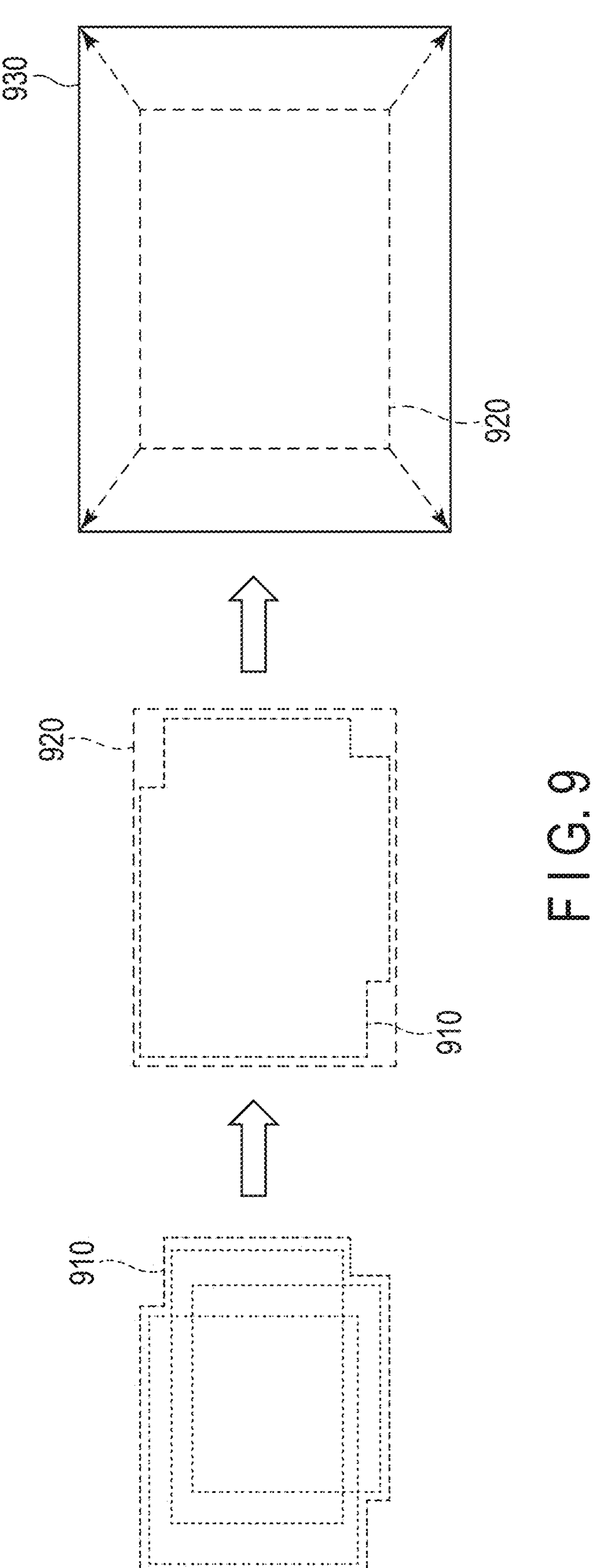
FIG. 9 is a diagram illustrating calculation of an ROI coordinate from a detection area.

FIG. 9 is a diagram illustrating calculation of an ROI coordinate from a detection area. FIG. 9 shows a detection area 910 corresponding to the detection area 722 shown in FIGS. 7 and 8, a rectangle 920 in contact with an outer perimeter of the detection area 910, and a region 930 of interest representing the rectangle 920 magnified at a predetermined magnification rate.

The processing circuitry 180 calculates the rectangle 920 based on the detection area 910. The processing circuitry 180 then magnifies the rectangle 920 at a predetermined magnification rate according to the type of the second display mode and calculates the region 930 of interest. The predetermined magnification rate is "1" or higher, and may be set discretionarily according to the type of the second display mode. For example, if the second display mode is the SWE mode, it suffices as long as the detection area includes an examination target; thus a predetermined magnification rate of "1" may be set so that the detection area and the region of interest have the same size.

The calculation of ROI coordinate data is not limited to the above. For example, ROI coordinate data of a region of interest may be calculated based on the center and the long side of the rectangle calculated based on the detection area. Also, when calculating a region of interest from the rectangle, at least one of the size or the shape of the region of interest may be changed. Changing the shape of the region of interest corresponds to, for example, differentiating a ratio between the long side and the short side (i.e., aspect ratio) of the rectangle from an aspect ratio of the region of interest.

(Step ST160)

After calculating the ROI coordinate, the processing circuitry 180 implements the display control function 187 to thereby display a ROI on second ultrasonic image data of the second display mode based on the ROI coordinate.

As described above, the ultrasound diagnostic apparatus according to the first embodiment acquires the first ultrasonic image data of the first mode, estimates the position of an examination target included in the first ultrasonic image data by applying a trained model to the first ultrasonic image data, outputs an estimation result, calculates a coordinate of a region of interest corresponding to the second mode based on the estimation result and the information on the second mode different from the first mode, and displays the region of interest on the second ultrasonic image data of the second mode based on the coordinate.

Since the ultrasound diagnostic apparatus according to the first embodiment can set an optimal ROI automatically regardless of mode transitioning type, it is unnecessary to manually set an ROI every time the mode transitions, allowing for reduced user burden.

The timing for starting the processing of automatically setting a region of interest and performing each processing is not limited to the processing illustrated in FIG. 3. For example, the processing of automatically setting a region of interest may be performed concurrently while the current first display mode is being executed. For example, in this case, the processing of step ST110 is omitted, and the processing of step ST120 is executed regardless of a user's instruction for execution. In response to an operation related to mode transition performed by a user, which corresponds to the processing of step ST110, the estimation processing of step ST130 may be performed, or the ROI coordinate calculation processing of step ST150 may be performed.

Each processing action of the ROI coordinate calculation processing is not limited to that shown in FIG. 4. For example, instead of the processing of step ST153 and step ST154, the processing circuitry 180 may select either a detection area including a unit of detection having the highest likelihood among one or more detection areas, or a detection area having the largest number of units of detection overlapping each other among one or more detection areas.

In the first embodiment, the case where the estimation result does not include an examination target is also considered; however, the embodiment is not limited thereto. For example, inclusion of an examination target in ultrasonic image data before transition may be premised. In this case, all the examination targets are included in the estimation result; thus, the processing of step ST140, for example, shown in FIG. 3 may be omitted.

Second Embodiment

The description provided in the first embodiment explains the processing for estimating the position of an examination target using a trained model and calculating a ROI coordinate based on the estimation result. On the other hand, a second embodiment will be described focusing on the processing for estimating a ROI coordinate using a trained model. The configuration of the ultrasound diagnostic apparatus according to the second embodiment is approximately the same as the configuration of the ultrasound diagnostic apparatus 1. Hereinafter, an overview of the processing according to the second embodiment will be described with reference to FIG. 10.

Figure 10:
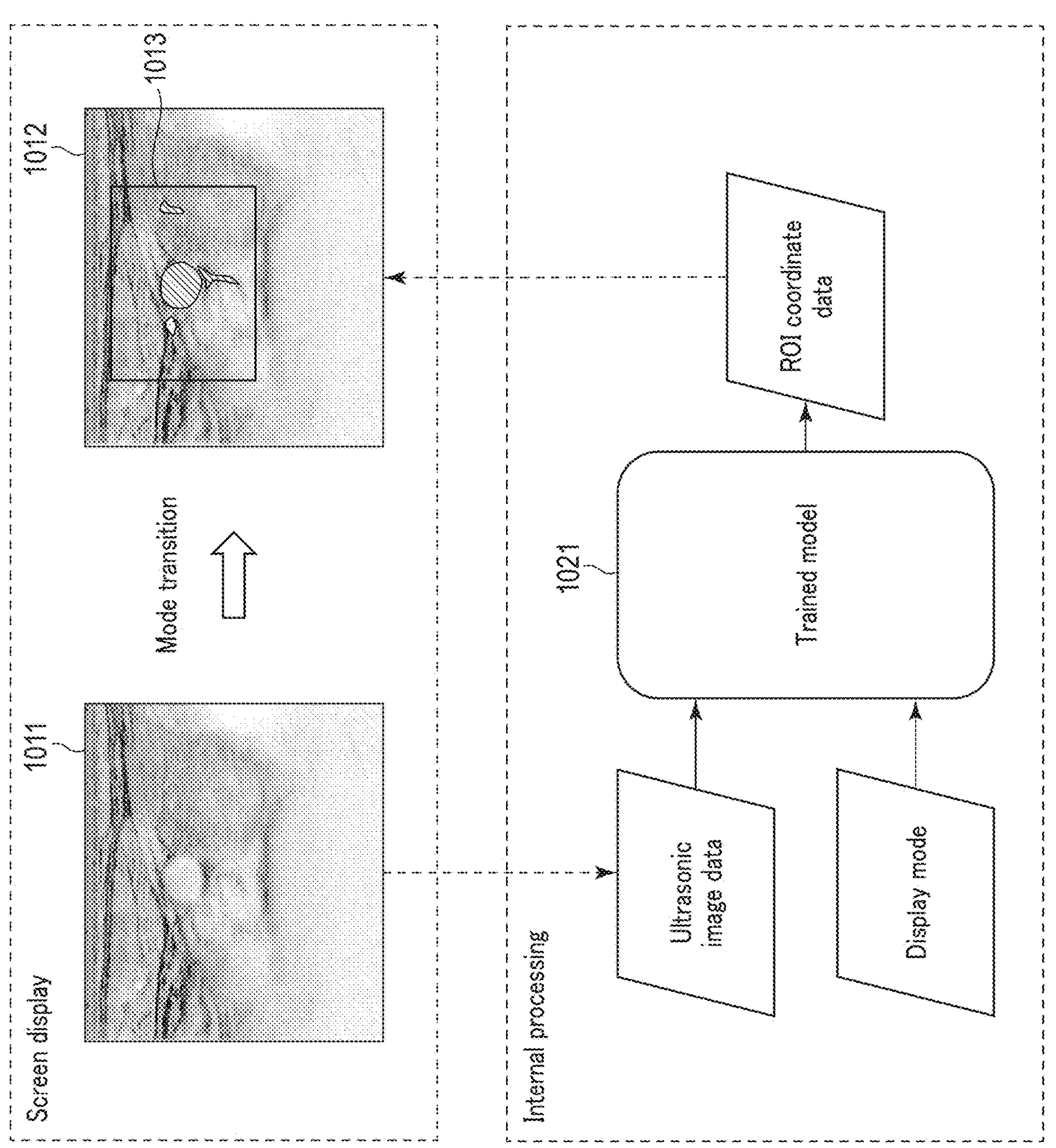
FIG. 10 is a diagram showing an example of screen display and internal processing related to the processing for automatically setting a region of interest of a second embodiment.

FIG. 10 is a diagram showing an example of screen display and internal processing related to the processing for automatically setting a region of interest of the second embodiment. FIG. 10 shows, as a display screen, an ultrasonic image 1011 and an ultrasonic image 1012 differing in the display mode before and after mode transition. FIG. 10 illustrates internal processing (processing of automatically setting a region of interest) performed during mode transition.

The screen display will be described first. The ultrasound diagnostic apparatus 1 according to the second embodiment changes the screen display from the ultrasonic image 1011 to the ultrasonic image 1012 in response to a mode-transition-related operation performed by a user. The ultrasonic image 1011 corresponds to the current display mode (which may be referred to as "a first display mode" and "a display mode before transition"). The ultrasonic image 1012 corresponds to a display mode after transition (which may be referred to as "a second display mode"). A ROI 1013 optimal to the second display mode is also displayed in the ultrasonic image 1012. The state during mode transition may be a state in which a screen update of the ultrasonic image 1011 is stopped, that is, a state approximately the same as a freeze state.

The internal processing will be described next. With the acquisition function 184, the processing circuitry 180, for example, acquires ultrasonic image data and information related to the display mode after transition, in response to an operation related to mode transition performed by a user. With the estimation function 185, the processing circuitry 180 applies a trained model 1021 to the ultrasonic image data and information on the display mode and outputs ROI coordinate data corresponding to the display mode after transition.

Figure 11:
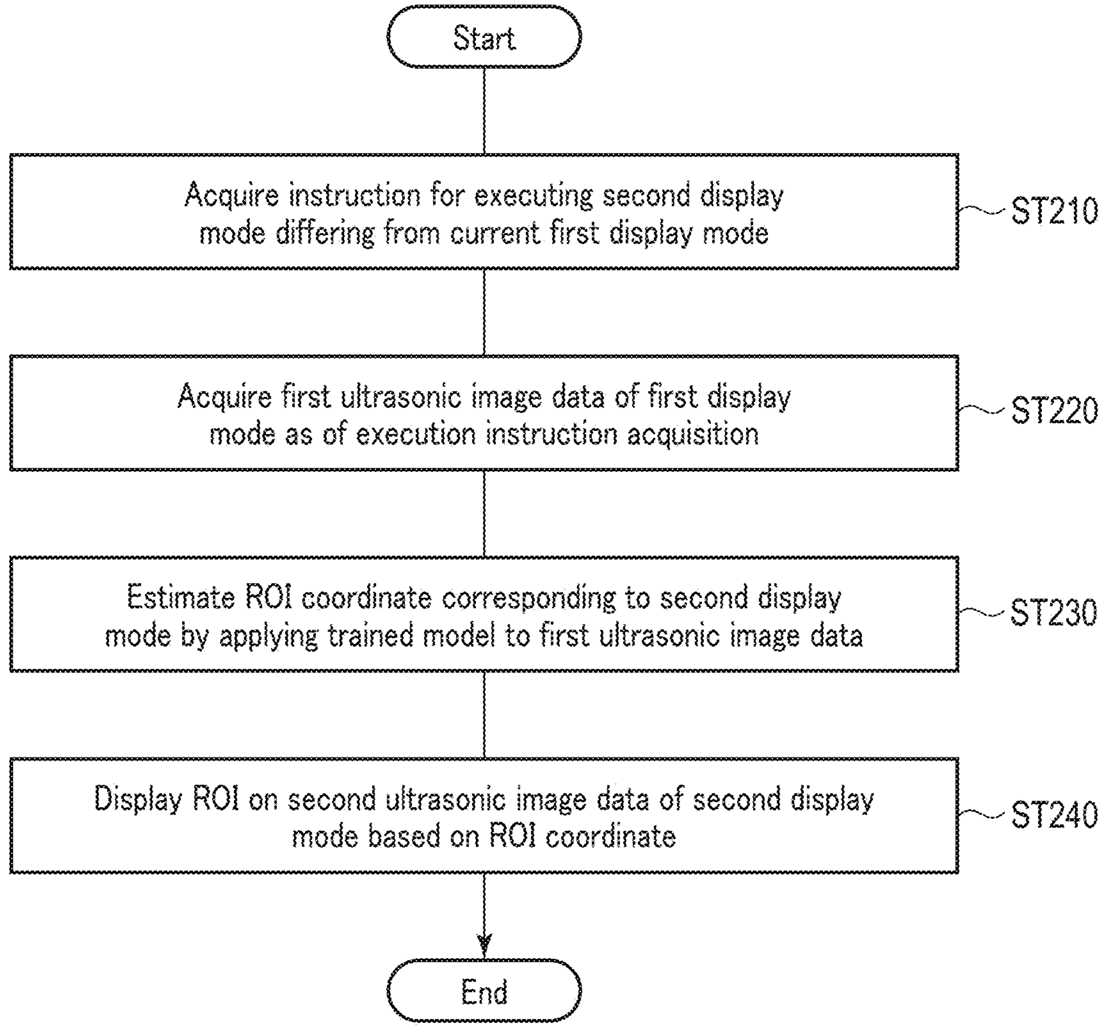
FIG. 11 is a flowchart showing an example of an operation of processing circuitry which executes the processing of automatically setting a region of interest of the second embodiment.

FIG. 11 is a flowchart showing an example of an operation for processing circuitry which executes the processing for automatically setting a region of interest of the second embodiment. The processing for automatically setting a region of interest shown in FIG. 11 is started, for example, in response to a mode-transition-related operation performed by a user. The mode-transition-related operation is, for example, an operation of executing a display mode different from the current display mode.

(Step ST210)

When the processing of automatically setting a region of interest starts, the processing circuitry 180 executes the acquisition function 184. When the processing circuitry 180 executes the acquisition function 184, the processing circuitry 180 acquires an instruction for executing a second display mode input by a user and differing from the current first display mode. In the descriptions provided hereinafter, the first display mode is the B-mode, and the second display mode is the bloodstream imaging mode.

(Step ST220)

After acquiring the execution instruction from the user, the processing circuitry 180 further acquires first ultrasonic image data of the first display mode as of the acquisition of the execution instruction. The first ultrasonic image data acquired may be video data including two or more frames.

(Step ST230)

After acquiring the first ultrasonic image data, the processing circuitry 180 executes the estimation function 185. When the processing circuitry 180 executes the estimation function 185, the processing circuitry 180 estimates a ROI coordinate corresponding to the second display mode by applying a trained model to the first ultrasonic image data. Specifically, the processing circuitry 180 estimates the position of an examination target included in the first ultrasonic image data by applying a trained model associated with the information on the second display mode to the first ultrasonic image data, and outputs a coordinate of a region of interest corresponding to the second display mode as an estimation result. The information on the second display mode is, for example, data in the form of one-hot vector representing the presence or absence of an element corresponding to the type of the display mode by "0" and "1". With regard to the trained model, each model may be prepared corresponding to display mode type, or a single model may be prepared regardless of display mode type.

(Step ST240)

After estimating the ROI coordinate, the processing circuitry 180 implements the display control function 187 to thereby display a ROI on second ultrasonic image data of the second display mode based on the ROI coordinate.

As described above, the ultrasound diagnostic apparatus according to the second embodiment acquires the first ultrasonic image data of the first mode and the information on the second mode different from the first mode, estimates the position of an examination target included in the first ultrasonic image data by applying a trained model associated with the information on the second mode to the first ultrasonic image data, outputs a coordinate of a region of interest corresponding to the second mode as an estimation result, and displays the region of interest on the second ultrasonic image data of the second mode based on the coordinate.

Since the ultrasound diagnostic apparatus according to the second embodiment can set an optimal ROI automatically regardless of the type of the mode transitioning, it is unnecessary to set an ROI manually every time the mode transitions, allowing for reduced user burden.

(Example of Display Screen)

Figure 12:
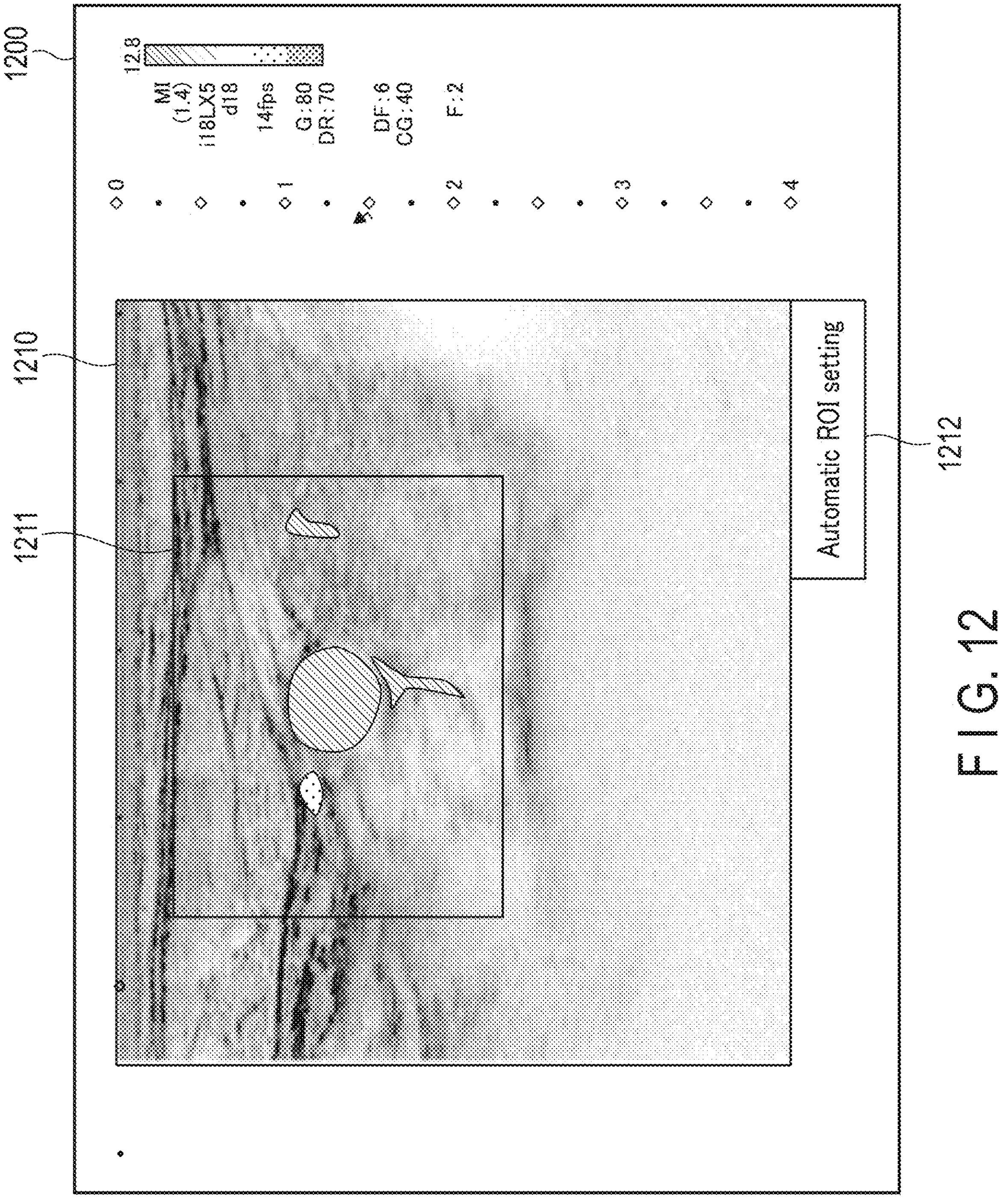
FIG. 12 is a diagram showing an example of a display screen after the processing for automatically setting a region of interest of the first embodiment and the second embodiment is performed.

FIG. 12 is a diagram showing an example of a display screen after the processing for automatically setting a region of interest of the first embodiment and the second embodiment is performed. A display screen 1200 shown in FIG. 12 displays an ultrasonic image 1210 obtained when a bloodstream imaging mode is selected as the second display mode. The ultrasonic image 1210 displays a ROI 1211. The display screen 1200 displays a character string 1212 "ROI Automatic Setting" indicating that a ROI has been automatically set by the processing for automatically setting a region of interest. In place of the character string, the display screen 1200 may display a mark (e.g., icon) indicating that automatic ROI setting has been performed. Also, by changing the color of ROI 1211, that is, the color of an outer frame of a region of interest, from a default color, whether or not automatic ROI setting has been performed may be presented. If the color of the outer frame is changed, the processing circuitry 180 may return it to a default color after the elapse of a predetermined time period, or at the timing when a user manually sets a ROI.

Other Embodiments

In the first embodiment and the second embodiment, for example, transition to a different imaging mode (such as from the B-mode to the bloodstream imaging mode) is assumed as mode transition; however, the present invention is not limited thereto. The mode transition according to another embodiment may include, for example, transition to a mode associated with the current display mode (such as a measuring mode).

Figure 13:
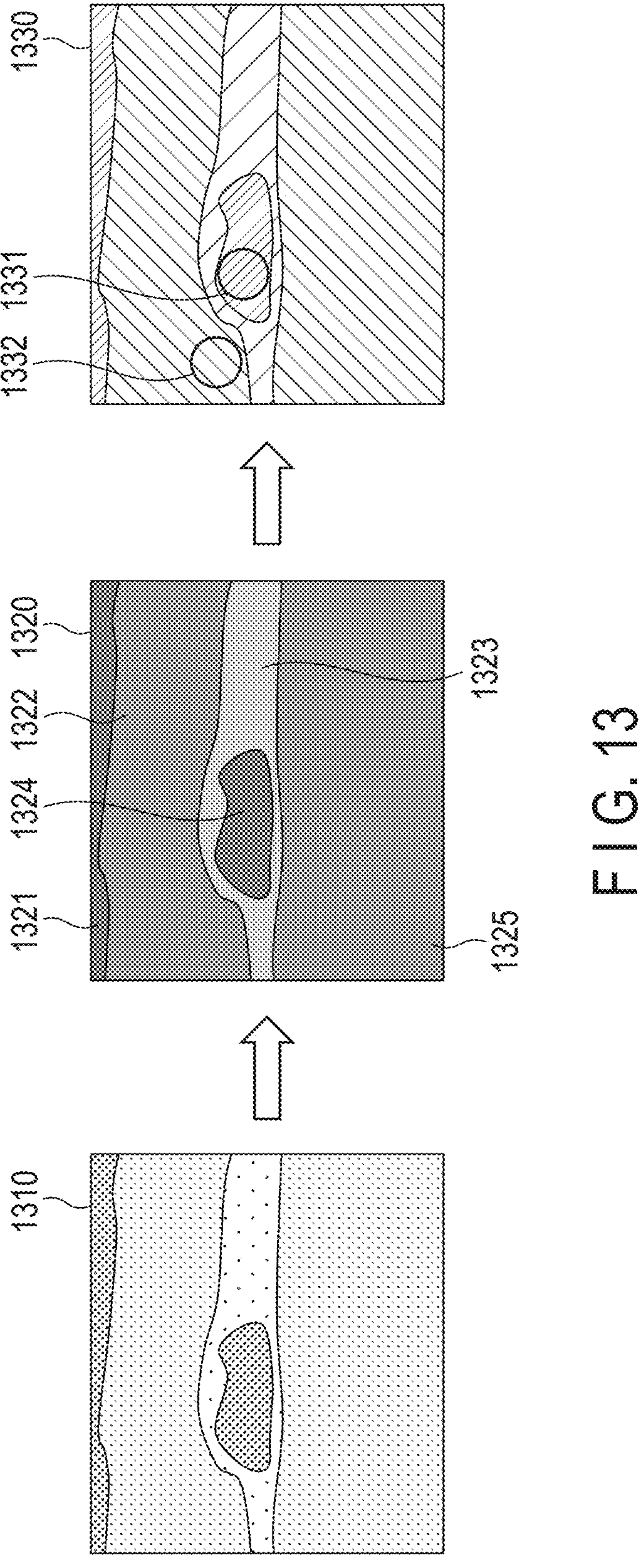
FIG. 13 is a diagram illustrating a first example related to processing for automatically setting a region of interest of another embodiment.

FIG. 13 is a diagram illustrating a first example related to the processing for automatically setting a region of interest of another embodiment. FIG. 13 shows an ultrasonic image 1310 displayed in the B-mode, a segmentation image 1320, and an ultrasonic image 1330 displayed in the strain elastography mode. In the first example shown in FIG. 13, the processing circuitry 180 performs image segmentation on the ultrasonic image 1310 and sets a measurement ROI according to the result of the segmentation. The scan ROI is set in advance.

If the ultrasonic image 1330 shows a region of the lacteal gland, for example, the processing circuitry 180 performs image segmentation related to the lacteal gland region on the ultrasonic image 1330, and generates the segmentation image 1320. The segmentation image 1320 shows five segmented regions 1321 to 1325, with which "skin", "fat", "lacteal gland", "tumor", and "pectoral major muscle" are associated, respectively.

After performing image segmentation, the processing circuitry 180 sets two measurement ROIs necessary to, for example, calculate a value of FLR (fat-lesion ratio) that compares a strain of fat and a strain of a pathological lesion based on the segmentation image 1320, which is the result of the segmentation. Specifically, the processing circuitry 180 automatically sets, in the ultrasonic image 1330, the measurement ROI 1331 related to the region 1324 showing "tumor" and a measurement ROI 1332 related to the region 1322 showing "fat".

Figure 14:
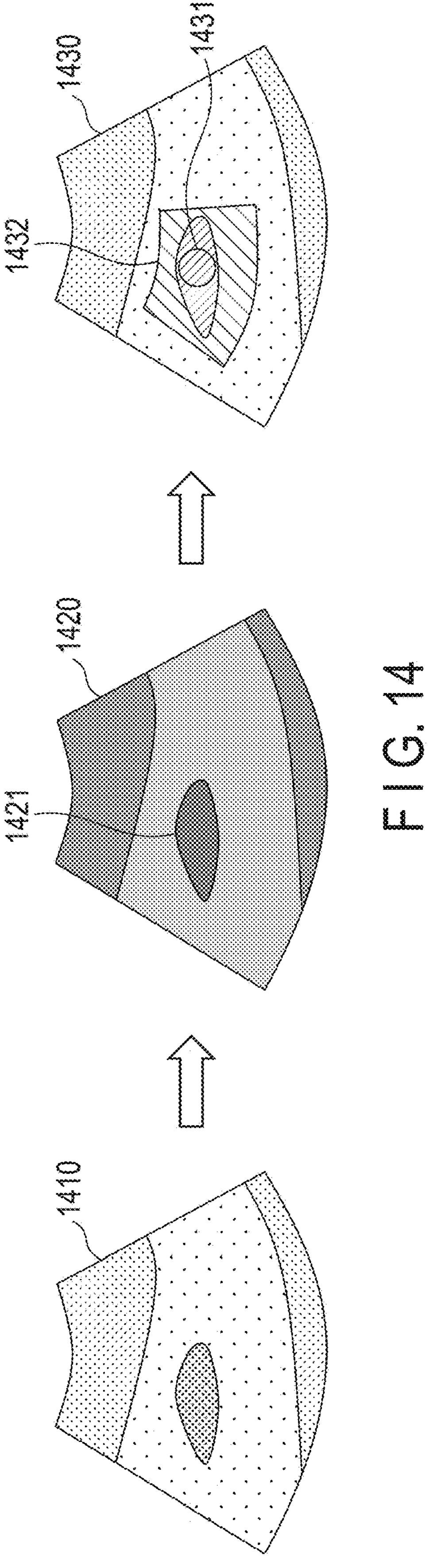
FIG. 14 is a diagram illustrating a second example related to the processing for automatically setting a region of interest of another embodiment.

FIG. 14 is a diagram illustrating a second example related to the processing for automatically setting a region of interest of another embodiment. FIG. 14 shows an ultrasonic image 1410 displayed in the B-mode, a segmentation image 1420, and an ultrasonic image 1430 displayed in the SWE mode. In the second example shown in FIG. 14, the processing circuitry 180 performs image segmentation on the ultrasonic image 1410 and sets a scan ROI and a measurement ROI according to the result of the segmentation. The scan ROI may be set in advance.

If the ultrasonic image 1410 includes a tumor, for example, the processing circuitry 180 performs image segmentation on the ultrasonic image 1410 and generates the segmentation image 1420. The segmentation image 1420 shows a plurality of segmented regions including a region 1421 showing the "tumor".

After performing image segmentation, the processing circuitry 180 automatically sets a scan ROI 1432 in SWE and, for example, a measurement ROI 1431 for measuring elasticity based on the segmentation image 1420, which is the result of the segmentation. The scan ROI 1432 may be set either in advance by a user, or automatically by the methods according to the first embodiment and the second embodiment.

Figure 15:
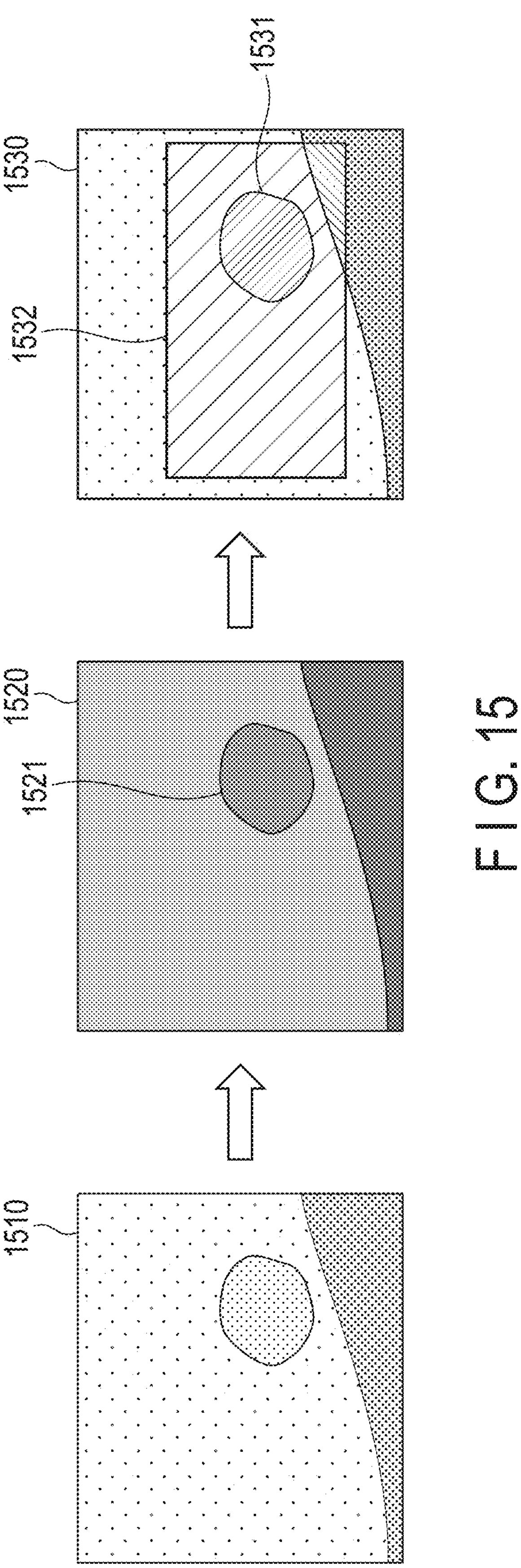
FIG. 15 is a diagram illustrating a third example related to the processing for automatically setting a region of interest of another embodiment.

FIG. 15 is a diagram illustrating a third example related to the processing for automatically setting a region of interest of another embodiment. FIG. 15 shows an ultrasonic image 1510 displayed in the B-mode, a segmentation image 1520, and an ultrasonic image 1530 displayed in the bloodstream imaging mode for low flow rate. In the third example shown in FIG. 15, the processing circuitry 180 performs image segmentation on the ultrasonic image 1510 and sets a scan ROI and a measurement ROI according to the result of the segmentation.

If the ultrasonic image 1510 includes a measurement target, for example, the processing circuitry 180 performs image segmentation on the ultrasonic image 1510 and generates the segmentation image 1520. The segmentation image 1520 shows a plurality of segmented regions including a region 1521 showing the "measurement target".

After performing image segmentation, the processing circuitry 180 automatically sets a scan ROI 1532 in the bloodstream imaging mode for low flow rate and, for example, a measurement ROI 1531 for calculating a vascular index of the measurement target based on the segmentation image 1520, which is the result of the segmentation. The scan ROI 1532 may be set either in advance by a user, or automatically by the methods according to the first embodiment and the second embodiment.

In each of the above embodiments, the ROI is automatically set by the processing for automatically setting a region of interest; however, the embodiments are not limited thereto. For example, with the system control function 188 (setting unit), the ultrasound diagnostic apparatus 1 may automatically change a parameter (e.g., image quality parameter) related to a mode after transition according to the position and the size of the ROI that are set. The image quality parameter is, for example, a transmission-reception frequency of an ultrasound beam, a focus position, a gain, and a depth. The ultrasound diagnostic apparatus 1 may be configured to be able to set whether or not to automatically change the image quality parameter together with automatically setting the ROI.

Third Embodiment

In the above embodiments, the configuration is described in which a region of interest is automatically set and shown in an ultrasonic image not showing a region of interest, in response to a user operation related to mode transition. On the other hand, in a third embodiment, a configuration is described in which a region of interest is reset and shown in an ultrasonic image showing a region of interest, in accordance with predetermined conditions, for example. Hereinafter, the processing for resetting a region of interest will be referred to as "processing for resetting a region of interest".

The reason for the necessity of resetting a region of interest is, for example, to resolve the screen display disorder caused by a change in an imaged cross-section. The causes of the change in the imaged cross-section are, for example, an ultrasonic probe and a living body. The change in the imaged cross-section due to an ultrasonic probe is caused, for example, when a site in contact with the ultrasonic probe is out of position, or a site in contact with the ultrasonic probe is changed. The change in the imaged cross-section due to a living body is caused, for example, when a site concerned with respiration, pulsation, or the like (such as an organ) moves. When a change in the imaged cross-section occurs, there will be a gap between an attention region in an ultrasonic image (e.g., a region for which it is desired to display an image of a bloodstream) and a region of interest set in an ultrasonic image (e.g., a region for which an image of a bloodstream is being displayed). Thus, a region of interest needs to be reset in order to resolve the screen display disorder caused by a gap between an attention region in an ultrasonic image and an image of a region of interest.

FIG. 16 is a block diagram showing a configuration example of an ultrasound diagnostic apparatus according to a third embodiment. The ultrasound diagnostic apparatus 1A shown in FIG. 16 includes an apparatus main body 100A and an ultrasonic probe 101. The apparatus main body 100A is connected to the input device 102 and the output device 103. The apparatus main body 100A is connected to an external device 104 via a network NW.

The apparatus main body 100A is an apparatus that generates an ultrasonic image based on a reflection wave signal received by the ultrasonic probe 101. The apparatus main body 100A includes ultrasound transmission circuitry 110, ultrasound reception circuitry 120, internal storage circuitry 130, an image memory 140, an input interface 150, an output interface 160, a communication interface 170, and processing circuitry 180A.

The processing circuitry 180A is, for example, a processor functioning as a center of the ultrasound diagnostic apparatus 1. The processing circuitry 180A implements the program stored in the internal storage circuitry 130, thereby realizing the functions corresponding to the program. The processing circuitry 180A includes, for example, a B-mode processing function 181, a Doppler processing function 182, an image generation function 183, an acquisition function 184 (acquisition unit), an estimation function 185 (estimation unit), a calculation function 186 (calculation unit), a display control function 187 (display controller), a system control function 188, and a resetting function 1600 (resetting unit).

The resetting function 1600 is a function for resetting a region of interest, which has already been set, according to predetermined conditions. Examples of the predetermined conditions include conditions concerning whether or not to recalculate the ROI coordinate (recalculation conditions), conditions concerning whether or not to reset the recalculated ROI coordinate (resetting conditions), conditions concerning whether or not to calculate a correlation value of the gap of the imaged cross-section (correlation-value calculating conditions), and conditions concerning whether or not to reset the ROI coordinate based on the calculated correlation value. The predetermined conditions also include the case where an instruction for resetting a region of interest is input by a user.

Specifically, with the resetting function 1600, the processing circuitry 180A, for example, determines whether or not to recalculate the ROI coordinate based on a recalculation condition. The recalculation condition is, for example, a frame interval for calculating a ROI coordinate. Therefore, by setting the frame interval to any number of 1 or more, the processing circuitry 180A can set so as to recalculate the ROT coordinate for each frame or for each set of frames.

In addition, with the resetting function 1600, the processing circuitry 180A, for example, determines whether or not to display a new ROI based on a resetting condition. The resetting condition is, for example, a threshold related to the degree of coincidence between a region of the current ROI coordinate and a region of the recalculated ROI coordinate. For example, the degree of coincidence being 100% means that there is no gap between the ROI coordinates before and after recalculation. For example, the lower the degree of coincidence, the larger the gap between the ROI coordinates before and after recalculation. A threshold may be set to any value according to an acceptable range of the gap. Thus, when the degree of coincidence falls below the threshold, the processing circuitry 180A can set so as to display a new ROI.

With the resetting function 1600, the processing circuitry 180A, for example, determines whether or not to calculate a correlation value based on a correlation-value calculating condition. The correlation value is a value related to correlation of two ultrasonic images (e.g., B-mode images) between two different frames. The correlation value may be calculated, for example, in a predetermined region (e.g., in an entire region or in a ROI) of the ultrasonic image. The correlation-value calculating condition is, for example, a frame interval for calculating a correlation value. Therefore, by setting the frame interval to any number of 1 or more, the processing circuitry 180A can set so as to calculate a correlation value for each frame or for each set of frames.

In addition, the processing circuitry 180A, for example, determines whether or not to recalculate the ROI coordinate and display a new ROI by comparing the correlation value and the threshold. The threshold may be set to any value according to the degree of correlation. Thus, when the correlation value falls below the threshold, the processing circuitry 180A can set so as recalculate the ROI coordinate and display a new ROI.

Hereinafter, two specific examples will be described as examples of the processing for resetting a region of interest. A first specific example is (1) a configuration of always displaying a new region of interest or (2) a configuration of displaying a new region of interest when satisfying the condition of resetting a ROI, after recalculating a ROI coordinate at predetermined frame intervals and based on the recalculated ROI coordinate. A second specific example is a configuration of recalculating a ROI coordinate when satisfying the condition of resetting a region of interest and displaying a new region of interest based on the recalculated ROI coordinate.

First Specific Example

FIG. 17 is a flowchart showing a first specific example of an operation of the processing circuitry which executes processing for resetting a region of interest of the third embodiment. The processing for resetting a region of interest shown in FIG. 17 is started, for example, after the processing of step ST160 in the flowchart shown in FIG. 3.

(Step ST310)

When the processing for resetting a region of interest is started, the processing circuitry 180A executes the resetting function 1600. When the processing circuitry 180A executes the resetting function 1600, the processing circuitry 180A determines whether or not the recalculation condition is satisfied. Specifically, the processing circuitry 180A determines whether or not the frame interval between the frame for which a ROI coordinate was calculated in the past and the current frame is a discretionary number. If the frame interval is a discretionary number, the processing circuitry 180A determines that the recalculation condition is satisfied and the processing proceeds to step ST320. If the frame interval is not a discretionary number, that is, if the frame interval is less than a discretionary number, the processing circuitry 180A determines that the recalculation condition is not satisfied and repeats the processing of step ST310 until the frame interval reaches a discretionary number.

(Step ST320)

After determining that the recalculation condition is satisfied, the processing circuitry 180A recalculates a ROI coordinate. Specifically, the processing circuitry 180A estimates the position of an examination target based on the B-mode image and recalculates a ROI coordinate based on the estimation result, as described in the first embodiment.

Alternatively, the processing circuitry 180A directly estimates (recalculates) a ROI coordinate based on the B-mode image, as described in the second embodiment.

(Step ST330)

After recalculating a ROI coordinate, the processing circuitry 180A implements the resetting function 1600 to determine whether or not the resetting condition is satisfied. Specifically, the processing circuitry 180A calculates the degree of coincidence between a region of the current ROI coordinate and a region of the recalculated ROI coordinate and determines whether or not the calculated degree of coincidence is less than the threshold. If the degree of coincidence is less than the threshold, the processing circuitry 180A determines that the resetting condition is satisfied and the processing proceeds to step ST340. If the degree of coincidence is not below the threshold, the processing circuitry 180A determines that the resetting condition is not satisfied and the processing returns to step ST310.

(Step ST340)

After determining that the resetting condition is satisfied, the processing circuitry 180A implements the display control function 187 to thereby display a new ROI on the ultrasonic image data based on the recalculated ROI coordinate.

The resetting condition in the above step ST330 is not limited to a comparison of the degree of coincidence concerning a region of a ROI coordinate. For example, the resetting condition may be a comparison between a threshold and a degree of coincidence concerning a region of the position of an examination target included in the estimation result, or a comparison between a threshold and a correlation value concerning the B-mode image data.

Second Specific Example

Figure 18:
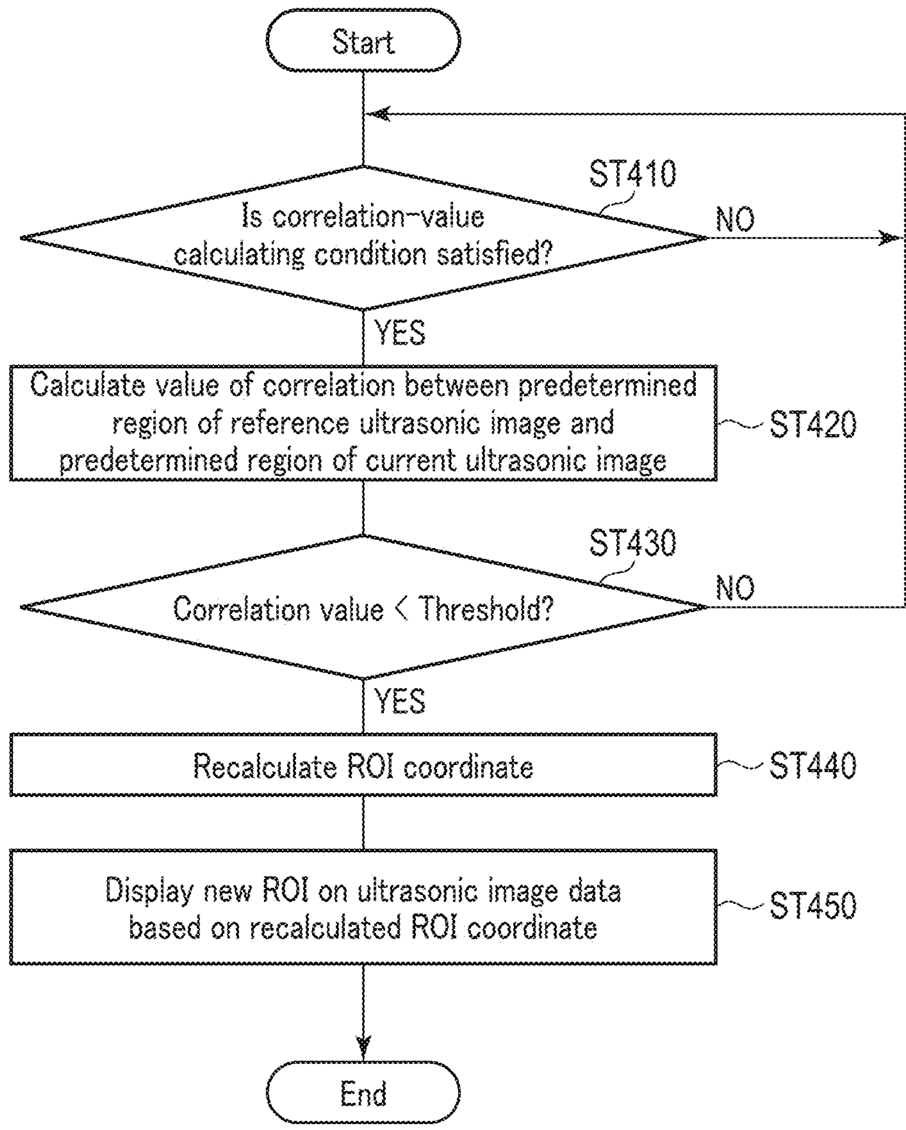
FIG. 18 is a flowchart showing a second specific example of a processing circuitry operation which executes the processing for resetting a region of interest of the third embodiment.

FIG. 18 is a flowchart showing a second specific example of an operation of the processing circuitry which executes the processing for resetting a region of interest of the third embodiment. The processing for resetting a region of interest shown in FIG. 18 is started, for example, after the processing of step ST160 in the flowchart shown in FIG. 3.

(Step ST410)

When the processing for resetting a region of interest is started, the processing circuitry 180A executes the resetting function 1600. When the processing circuitry 180A executes the resetting function 1600, the processing circuitry 180A determines whether or not the correlation-value calculating condition is satisfied. Specifically, the processing circuitry 180A determines whether or not the frame interval between a reference frame and the current frame is a discretionary number. If the frame interval is a discretionary number, the processing circuitry 180A determines that the correlation-value calculating condition is satisfied and the processing proceeds to step ST420. If the frame interval is not a discretionary number, that is, if the frame interval is less than a discretionary number, the processing circuitry 180A determines that the correlation-value calculating condition is not satisfied, and repeats the processing of step ST410 until the frame interval reaches a discretionary number.

(Step ST420)

After determining that the correlation-value calculating condition is satisfied, the processing circuitry 180A calculates a value of correlation between a predetermined region of a reference ultrasonic image and a predetermined region of the current ultrasonic image. The reference ultrasonic image is, for example, an ultrasonic image frame with a newly set or reset ROI differing from the previously set ROI. The reference ultrasonic image may use, as a reference, an ultrasonic image frame coming prior to the current ultrasonic image frame by a predetermined number of frames.

(Step ST430)

After calculating the correlation value, the processing circuitry 180A determines whether or not the correlation value is less than the threshold. If it is determined that the correlation value is less than the threshold, the processing proceeds to step ST440. If it is determined that the correlation value is greater than the threshold, the processing returns to step ST410.

(Step ST440)

After determining that the correlation value is less than the threshold, the processing circuitry 180A recalculates a ROI coordinate. The recalculation is the same as that performed in step ST320 shown in FIG. 17.

(Step ST450)

After recalculating a ROI coordinate, the processing circuitry 180A implements the display control function 187 to thereby display a new ROI on the ultrasonic image data based on the recalculated ROI coordinate.

As described above, the ultrasound diagnostic apparatus according to the third embodiment can reset a region of interest according to predetermined conditions, and thus can appropriately display a region of interest even when an imaged cross-section is changed.

According to at least one embodiment described above, it is possible to automatically set an optimal ROI regardless of the type of the transitioning mode.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus, comprising:

processing circuitry configured to:

acquire first ultrasonic image data of a first display mode;

in response to receiving, while the first ultrasonic image data of the first display mode is displayed on a display, an instruction to execute a second display mode different from the first display mode:

estimate a position of an examination target included in the first ultrasonic image data by applying a trained model to the first ultrasonic image data and output an estimation result including the estimated position;

calculate coordinates representing a position and a size of a region of interest surrounding the examination target based on the estimated position of the examination target and a type of the second display mode; and display, on second ultrasonic image data of the second display mode displayed on the display, the region of interest having the position and the size represented by the calculated coordinates.

2. The ultrasound diagnostic apparatus according to claim 1, wherein the estimation result includes one or more units of detection including the examination target, and the processing circuitry is further configured to:
determine one or more detection areas based on the one or more units of detection; and
calculate the coordinates based on one most probable detection area from among the determined one or more detection areas.

3. The ultrasound diagnostic apparatus according to claim 2, wherein the processing circuitry is further configured to, when a plurality of detection areas among the determined one or more detection areas are determined:
calculate a total value of a likelihood of those units of detection, of the one or more units of detection, included in each of the determined plurality of detection areas, based on a corresponding likelihood of each of the one or more units of detection obtained when estimating the position of the examination target; and
determine, as the one most probable detection area, a particular detection area having a highest total likelihood value among the determined plurality of detection areas.

4. The ultrasound diagnostic apparatus according to claim 2, wherein the processing circuitry is further configured to, when a plurality of detection areas among the determined one or more detection areas are determined,
determine, as the one most probable detection area, a particular detection area including a particular unit of detection, of the one or more units of detection, having a highest likelihood, among the determined plurality of detection areas, based on a likelihood of the one or more units of detection obtained when estimating the position of the examination target.

5. The ultrasound diagnostic apparatus according to claim 2, wherein the processing circuitry is further configured to, when a plurality of detection areas among the determined one or more detection areas are determined, determine, as the one most probable detection area, a detection area having a largest number of units of detection, of the one or more units of detection, overlapping each other, among the determined plurality of detection areas.

6. The ultrasound diagnostic apparatus according to claim 2, wherein the determined one most probable detection area is a single unit of detection, of the one or more units of detection, or a plurality of units of detection, of the one or more units of detection.

7. The ultrasound diagnostic apparatus according to claim 6, wherein the processing circuitry is further configured to, when the determined one most probable detection area is the plurality of units of detection, calculate the coordinates based on a rectangle in contact with an outer perimeter of the plurality of units of detection.

8. The ultrasound diagnostic apparatus according to claim 7, wherein the processing circuitry is further configured to calculate the coordinates based on a center and a long side of the rectangle.

9. The ultrasound diagnostic apparatus according to claim 1, wherein the processing circuitry is further configured to change at least one of the size or a shape of the region of interest according to information on the second display mode.

10. The ultrasound diagnostic apparatus according to claim 1, wherein the processing circuitry is further configured to reset the region of interest according to a predetermined condition.

11. The ultrasound diagnostic apparatus according to claim 10, wherein the processing circuitry is further configured to:
calculate new coordinates of a new region of interest in a frame after a frame for which the coordinates of the region of interest are calculated;
reset the new region of interest when a degree of coincidence between a region of the coordinates and a region of the new coordinates is less than a threshold; and
display the new region of interest on the second ultrasonic image data.

12. The ultrasound diagnostic apparatus according to claim 10, wherein the processing circuitry is further configured to:
calculate a value of correlation between a predetermined region of reference ultrasonic image data and a predetermined region of current ultrasonic image data;
determine to reset a new region of interest when the value of correlation is less than a threshold;
calculate new coordinates of the new region of interest based on the current ultrasonic image data; and
display the new region of interest on the second ultrasonic image data.

13. The ultrasound diagnostic apparatus according to claim 1, wherein the processing circuitry is further configured to calculate the coordinates in response to a mode-transition-related user operation.

14. The ultrasound diagnostic apparatus according to claim 1, wherein the processing circuitry is further configured to acquire the first ultrasonic image data in response to a mode-transition-related user operation.

15. The ultrasound diagnostic apparatus according to claim 1, wherein the processing circuitry is further configured to estimate the position of the examination target in response to a mode-transition-related user operation.

16. The ultrasound diagnostic apparatus according to claim 1, wherein the processing circuitry is further configured to change a color of an outer frame of the region of interest according to the estimation result.

17. The ultrasound diagnostic apparatus according to claim 1, wherein the processing circuitry is further configured to display at least one of a character string or a mark on a display screen of the second display mode according to the estimation result.

18. The ultrasound diagnostic apparatus according to claim 1, wherein the second display mode is a bloodstream imaging mode or an elastography mode.

19. The ultrasound diagnostic apparatus according to claim 18, wherein the second display mode is a measurement mode associated with the bloodstream imaging mode or the elastography mode, and the region of interest shows a measurement region.

20. The ultrasound diagnostic apparatus according to claim 1, wherein the processing circuitry is further configured to change a parameter related to the second display mode according to the position of the region of interest.

21. The ultrasound diagnostic apparatus according to claim 20, wherein the processing circuitry is further configured to change any one of a transmission-reception frequency of an ultrasound beam, a focus position, a gain, and a depth as the parameter.

22. The ultrasound diagnostic apparatus according to claim 1, wherein the trained model is a deep neural network.

23. An ultrasound diagnostic apparatus comprising processing circuitry configured to:
acquire first ultrasonic image data of a first display mode and information of a second display mode different from the first display mode;

acquire an instruction to execute the second display mode while the first ultrasonic image data is displayed on a display;

estimate a position of an examination target included in the first ultrasonic image data by applying a trained model to the first ultrasonic image data and the information on the second display mode and output coordinates representing a position and a size of a region of interest surrounding the examination target based on the estimated position of the examination target and a type of the second display mode;

acquire second ultrasonic image data by executing the second display mode; and display, on the second ultrasonic image data of the second display mode, the region of interest having the position and the size represented by the calculated coordinates.

24. The ultrasound diagnostic apparatus according to claim 23, wherein the processing circuitry is further configured to reset the region of interest according to a predetermined condition.

25. The ultrasound diagnostic apparatus according to claim 24, wherein the processing circuitry is further configured to:

estimate new coordinates of a new region of interest in a frame after a frame for which the coordinates of the region of interest are estimated;

reset the new region of interest when a degree of coincidence between a region of the coordinates and a region of the new coordinates is less than a threshold; and display the new region of interest on the second ultrasonic image data.

26. The ultrasound diagnostic apparatus according to claim 24, wherein the processing circuitry is further configured to:

calculate a value of correlation between a predetermined region of reference ultrasonic image data and a predetermined region of current ultrasonic image data;

determine to reset a new region of interest when the value of correlation is less than a threshold;

estimate new coordinates of the new region of interest based on the current ultrasonic image data; and display the new region of interest on the second ultrasonic image data.

* * * * *